(12) United States Patent
Akashi et al.

(10) Patent No.: US 8,496,373 B2
(45) Date of Patent: Jul. 30, 2013

(54) METHOD OF INFRARED INSPECTION FOR STRUCTURE, TEST SPECIMEN FOR INFRARED INSPECTION AND HEAT CONDUCTIVE MEMBER

(75) Inventors: Yukio Akashi, Takamatsu (JP); Kazuaki Hashimoto, Takamatsu (JP); Shogo Hayashi, Takamatsu (JP)

(73) Assignee: West Nippon Expressway Engineering Shikoku Company Limited, Takamatsu-shi (JP)

( * ) Notice: Subject to any disclaimer, the term of this patent is extended or adjusted under 35 U.S.C. 154(b) by 358 days.

(21) Appl. No.: 12/864,965

(22) PCT Filed: Aug. 24, 2009

(86) PCT No.: PCT/JP2009/064710
§ 371 (c)(1),
(2), (4) Date: Jul. 28, 2010

(87) PCT Pub. No.: WO2010/089913
PCT Pub. Date: Aug. 12, 2010

(65) Prior Publication Data
US 2011/0058154 A1 Mar. 10, 2011

(30) Foreign Application Priority Data
Feb. 3, 2009 (WO) .................. PCT/JP2009/051772

(51) Int. Cl.
G01N 25/00 (2006.01)
G01N 17/00 (2006.01)
G01J 5/00 (2006.01)

(52) U.S. Cl.
USPC .......... 374/4; 374/5; 374/7; 374/121; 374/45; 374/57; 374/124

(58) Field of Classification Search
USPC .......................... 374/4, 5, 7, 121, 45, 57, 124
See application file for complete search history.

(56) References Cited

U.S. PATENT DOCUMENTS

2010/0074515 A1* 3/2010 Zhao et al. .................... 382/149
2011/0071769 A1* 3/2011 Akashi et al. .................. 702/35

FOREIGN PATENT DOCUMENTS

JP 2855366 B2 2/1999
JP 2004-117238 A1 4/2004

(Continued)

OTHER PUBLICATIONS

Translations of JP2005-140622, JP2004-117238, JP2006-329760, JP2005-291743.*

(Continued)

Primary Examiner — Mirellys Jagan
(74) Attorney, Agent, or Firm — Kratz, Quintos & Hanson, LLP

(57) ABSTRACT

A test specimen having a to-be-photographed surface and an attachment surface which is a back side thereof is produced, and attached to a structure. An artificial abnormal portion is provided between a to-be-inspected surface of the structure and the to-be-photographed surface of the test specimen. The to-be-photographed surface of the test specimen is photographed by the infrared camera. When a surface temperature difference between the abnormal and the sound portions increases to a certain level on the to-be-photographed surface, it is capable of discriminating between the abnormal and the sound portions by an infrared thermal image of the test specimen. In a time zone in which discriminating between the abnormal and the sound portions is capable, the to-be-inspected surface of the structure is photographed by the infrared camera. If there is a damage in the surface layer of the structure, a damaged position can be discriminated by an infrared thermal image.

9 Claims, 21 Drawing Sheets

| FOREIGN PATENT DOCUMENTS | | |
|---|---|---|
| JP | 2005-140622 A1 | 6/2005 |
| JP | 2005-291743 A1 | 10/2005 |
| JP | 2006-329760 A1 | 12/2006 |
| JP | 2007-149725 A1 | 6/2007 |
| JP | 2008-135542 A1 | 6/2008 |

OTHER PUBLICATIONS

International Search Report for International Application No. PCT/JP2009/064710 dated Oct. 19, 2009.

* cited by examiner

METHOD OF INFRARED INSPECTION FOR STRUCTURE, TEST SPECIMEN FOR INFRARED INSPECTION AND HEAT CONDUCTIVE MEMBER

TECHNICAL FIELD

The present invention relates to a method of infrared inspection of inspecting a structure for defects by means of an infrared camera, and more particularly to a method of inspecting a heat environment of a structure by taking a picture of a test specimen representing the structure by an infrared camera. The invention also relates to the test specimen and a heat conductive member which is interposed between the structure and the test specimen.

BACKGROUND ART

A concrete structure represented by a bridge and an elevated bridge (hereinafter, simply called a "structure") is influenced by a weather change, ground deformation, and load bearing, in addition to its own deterioration over the years. When they are collected and bad conditions overlap, the structure may partially break down or peel, for example, possibly leading to a damage to or an accident on a third party. Accordingly, the structure is required to be inspected and observed constantly in order to prevent occurrence of flaking of the structure.

As a method for inspection and observation of the structure, there has been studied a method of infrared inspection which is capable of inspecting the structure in a wide range with high efficiency without necessity of approaching the structure. FIG. 13 shows the time course of changes in three temperatures, namely an atmosphere temperature, a surface temperature of a sound portion of the structure, and a surface temperature of an abnormal portion of the structure. As shown in FIG. 13, a difference is produced between the surface temperature of the abnormal portion and the surface temperature of the sound portion with a change of the heat environment of the structure and the heat environment around it (the atmosphere temperature change here).

FIGS. 14A and 14B show a concept of a phenomenon that a temperature difference is produced. FIG. 14A shows a state of daytime, and FIG. 14B shows a state of nighttime. As shown in FIG. 14A, the atmosphere temperature is higher than the temperature of a concrete 80 in a time zone t1 of FIG. 13, and heat is conducted from outside to inside of the concrete 80. Since the heat conduction is blocked at an abnormal portion 81, the heat conducted from the outside of the concrete 80 remains in a surface portion 82 between the concrete surface and the abnormal portion. As a result, the temperature of a front surface 83 of the surface portion 82 where the abnormal portion 81 is present (this is called "the surface temperature of the abnormal portion 81") becomes higher than the surface temperature around it. As shown in FIG. 14B, the atmosphere temperature is lower than the temperature of the concrete 80 in a time zone t2 of FIG. 13, and heat is conducted from inside to outside of the concrete 80. Since heat conduction is blocked at the abnormal portion 81, the heat conducted from the inside of the concrete 80 is not conducted to the surface portion 82 which is between the concrete surface and the abnormal portion 81. As a result, the surface temperature of the abnormal portion 81 becomes lower than the surface temperature around it. The method of infrared inspection uses the above phenomenon, and measures the surface temperature of the structure by the infrared camera and discriminates between the sound portion and the abnormal portion by using the temperature difference.

The method of infrared inspection can find the abnormal portion when the temperature difference between the sound portion and the abnormal portion is large to some extent but cannot find the abnormal portion when the temperature difference between the sound portion and the abnormal portion is small. Therefore, it is important to perform the infrared inspection in the heat environment where there is a temperature difference between the sound portion and the abnormal portion. Conventionally, the following methods are used to find such a heat environment.

(1) Method for Estimation of Heat Environment by Atmosphere Temperature Observation This method estimates whether or not the environment is suitable for infrared inspection by measuring the atmosphere temperature around the structure to be measured.

(2) Heat Environment Assessment Method Using Test Specimen

As shown in FIG. 15, this method assesses whether or not the heat environment of a structure 90 is suitable for infrared inspection by disposing in the vicinity of the structure 90 concrete blocks which are artificially and partly formed with an abnormal portion to represent the structure 90 to be measured, namely test specimens 91, 92 and 93, taking pictures of the test specimens 91, 92 and 93 by an infrared camera, and checking the abnormal portion on the photographed infrared thermal images. The test specimen 91 is disposed just below the structure, the test specimen 92 is disposed at a position which is in the sun during an afternoon time zone, and the test specimen 93 is disposed at a position which is in the sun during a morning time zone. The test specimen 91 is a concrete block placed in an instrument shelter, but the test specimens 92 and 93 are concrete blocks exposed. This type of method is disclosed in, for example, the following Patent References 1 and 2.

Patent Reference 1: JP 2005-140622 A
Patent Reference 2: JP 2006-329760 A

DISCLOSURE OF THE INVENTION

Problems to be Solved by the Invention

According to the above method (1), a daily range which is a difference between the maximum atmosphere temperature and the minimum atmosphere temperature in a day is mainly used, and when the daily range is large, it is determined that the heat environment is suitable for infrared inspection. But, it is known that even if the daily range is small, the infrared inspection can be made when there is an abrupt temperature change, and conversely, even if the daily range is large, the heat environment becomes unsuitable for the infrared inspection when a temperature change is moderate. Therefore, it is hard to say that the above method (1) is a quantitative method for estimation of heat environment.

Meanwhile, since the above method (2) uses a test specimen which represents a structure to be measured in order to grasp the heat environment, its accuracy is higher than the above method (1), and it can be said that the above method (2) is a quantitative assessment method for the heat environment. And, it can be said that the above method (2) is a superior method in view of the following points that even when a bridge does not have a scaffold, the test specimen can be disposed under a beam, and the installation position of the test specimen is not so restricted.

But, according to the present inventors, it was found that the above method (2) had an aspect that it was hard to grasp the heat environment. In a case where the heat environment at the undersurface of the bridge is to be found out, the test specimen is disposed below a beam according to the above method (2). In this state, a factor affecting on the temperature of the test specimen is a change in the atmosphere temperature only. In the case of a structure having a large member-thickness, such as a hollow slab bridge or the like, a factor affecting on the temperature of the bridge undersurface is mainly a change in the atmosphere temperature only, and since the heat environment of the bridge becomes substantially equivalent to the heat environment of the test specimen, the above method (2) has high accuracy of grasping the heat environment. But, in a case of a structure having a small member-thickness such as a concrete floor slab bridge, a concrete box girder or the like, the bridge itself tends to be effected by solar radiation, wind and the like in addition to the atmosphere temperature, and there occurs a case that the heat environment of the bridge is different from the heat environment of the test specimen, so that the accuracy of grasping the heat environment by the above method (2) becomes low.

In particular, it is known that when a structure having a member-thickness of less than 30 cm undergoes the infrared inspection, it is indirectly affected by an influence of a solar radiation amount in addition to an influence of the atmosphere temperature. A correspondence relationship between the bridge and the influence of the solar radiation energy is shown in Table 1.

TABLE 1

| Bridge to be inspected | | Influence of solar radiation energy | | |
| --- | --- | --- | --- | --- |
| Bridge type | Portion | Direct effect | Indirect effect | Remarks |
| Steel bridge | Concrete floor slab portion (t = 25 cm or below) | x | ○ | |
| All types of bridges | Wall parapet portion | ○ | ○ | (Southward) |

The "direct effect" and the "indirect effect" in Table 1 are described with reference to FIG. 16. The "direct effect" means a phenomenon that a front surface 80a of the concrete 80 is affected by the sunlight which directly shines the front surface 80a of the concrete 80, namely a to-be-inspected surface and to-be-photographed surface. The "indirect effect" means a phenomenon that the front surface 80a of the concrete 80 is affected by the sunlight to which a back surface 80b of the concrete 80 is exposed. In a broad sense, the "direct effect" means a phenomenon that the front surface 80a of the concrete 80 is affected by the heat which is on the side of the front surface 80a of the concrete 80, and the "indirect effect" means a phenomenon that the front surface 80a of the concrete 80 is affected by the heat which is on the side of the back surface 80b of the concrete 80.

As shown in FIG. 16, in the surface temperature of the structure which receives the indirect effect, the surface temperature of the abnormal portion becomes lower than the surface, temperature of the sound portion. This is because the relationship between the concrete 80 and the atmosphere temperature on the side of the front surface 80 becomes the same as the situation shown in FIG. 14B. In other words, by the solar radiation to the back surface 80b, the temperature in the concrete 80 becomes higher than an outside air temperature on the side of the front surface 80a, and the heat is conducted from inside of the concrete 80 toward the front surface 80a. At this time, the heat conduction is blocked at the abnormal portion 81, so that the heat conducted from the inside of the concrete 80 is not conducted to the surface portion 82 between the front surface 80a and the abnormal portion 81. As a result, the surface temperature of the abnormal portion 81 becomes lower than the surface temperature around it.

Thus, to perform the infrared inspection for the structure having a small member-thickness, it is necessary to consider the heat environment including the influence of the indirect effect, but it is hard to grasp the heat environment including the indirect effect by using the test specimen used in the above-described method (2). The reason is described below with reference to FIG. 17.

FIG. 17A shows temperature measurement positions of a steel bridge having a concrete floor slab, and FIG. 17B shows temperature changes and solar radiation amount changes at the respective temperature measurement positions of FIG. 17A with a lapse of time. FIG. 17B shows a time lag of about six hours between a peak of the atmosphere temperature within the instrument shelter and a peak of a concrete floor slab undersurface temperature and the atmosphere temperature just below the concrete floor slab. In other words, it is seen that there is a difference in tendency of the temperature change between the concrete floor slab and the test specimen within the instrument shelter. Thus, a difference is developed among the temperature peaks. A major cause of this is the following phenomenon. When a pavement on the concrete top surface is heated by solar radiation, heat conduction occurs from an upper portion to a lower portion of the concrete, and when the concrete floor slab has a small member-thickness, the heat is conducted to the lower portion of the concrete, thereby increasing the temperature of the floor slab undersurface. The difference is developed among the temperature peaks according to the time duration for this heat conduction.

The present invention has been made in view of the above circumstances and makes it possible to grasp accurately a heat environment of a structure to be inspected even if complex conditions overlap in infrared inspection.

Means for Solving the Problem

A first aspect of the invention is a method of infrared inspection of inspecting a structure for defects by using an infrared camera, comprising:

a test specimen attaching step of preparing a plate-shaped test specimen having a to-be-photographed surface and an attachment surface which is a back side of the to-be-photographed surface, attaching the test specimen to the structure with a to-be-inspected surface of the structure and the attachment surface of the test specimen opposed to each other, and providing an artificial abnormal portion between the to-be-inspected surface of the structure and the to-be-photographed surface of the test specimen;

a test specimen photographing step of photographing the to-be-photographed surface of the test specimen by the infrared camera;

a discriminating step of discriminating between a surface of the abnormal portion and a surface of a sound portion excepting the abnormal portion on the to-be-photographed surface of the test specimen by using an infrared thermal image of the test specimen; and a structure photographing step of photographing the to-be-inspected surface of the structure by the infrared camera in a time zone in which it is capable of discriminating between the surface of the abnormal portion and the surface of the sound portion.

As a second aspect of the invention, the test specimen attaching step prepares the plate-shaped test specimen having the to-be-photographed surface and the attachment surface which is the back side of the to-be-photographed surface in which the abnormal portion is formed on the side of the attachment surface, and attaches the test specimen to the structure with the to-be-inspected surface of the structure and the attachment surface of the test specimen opposed to each other.

The first aspect of the invention is described with reference to the second aspect of the invention.

As a preparatory stage of the infrared inspection, the plate-shaped test specimen having the to-be-photographed surface and the attachment surface which is the back side of the to-be-photographed surface and formed with the abnormal portion on its attachment surface side is prepared. And, the test specimen is attached to the structure with the to-be-inspected surface of the structure and the attachment surface of the test specimen opposed to each other (test specimen attaching step).

In a case where the to-be-inspected surface of the structure is actually photographed by the infrared camera, the to-be-photographed surface of the test specimen is photographed by the infrared camera (test specimen photographing step).

In the to-be-photographed surface of the test specimen, when a difference between the surface temperature of the abnormal portion and the surface temperature of the sound portion other than the abnormal portion becomes large to a certain level, it becomes possible to discriminate between the surface of the abnormal portion and the surface of the sound portion by using the infrared thermal image of the photographed test specimen (discriminating step).

In the time zone when it has become possible to discriminate between the surface of the abnormal portion and the surface of the sound portion, the to-be-inspected surface of the structure is photographed by the infrared camera (structure photographing step).

If the surface layer of the to-be-inspected surface of the structure has a damage, the position of the damage can be checked by using an infrared thermal image of the to-be-inspected surface.

As a third aspect of the invention, the test specimen attaching step interposes a heat conductive member between the to-be-inspected surface of the structure and the attachment surface of the test specimen.

When the heat conductive member is interposed between the test specimen and the structure as in the third aspect of the invention, the heat conduction from the structure to the test specimen becomes smooth, and a degree of adhesion between the test specimen and the structure becomes high.

According to a fourth aspect of the invention, a depression corresponding to the abnormal portion is formed in a part of the attachment surface of the test specimen.

The fourth aspect of the invention relates to an embodiment of the abnormal portion formed in the test specimen. The depression can be produced with ease.

According to a fifth aspect of the invention, the structure conducts heat received by the back side of the to-be-inspected surface to the to-be-inspected surface.

The fifth aspect of the invention relates to an embodiment of the structure to be inspected. When the test specimen is directly attached to the structure which induces a so-called indirect effect that conducts the heat received by the back side of the to-be-inspected surface to the to-be-inspected surface, the test specimen also induces the same indirect effect.

Namely, the heat environment of the structure can be grasped more accurately than when the test specimen is disposed in the vicinity of the structure.

According to a sixth aspect of the invention, the test specimen attaching step attaches plural test specimens each having a different state of the abnormal portion to the structure.

When the plural test specimens each having a different state of the abnormal portion are attached to the structure and the each test specimen is photographed by the infrared camera as in the sixth aspect of the invention, there may occur a situation that the abnormal portion and the sound portion can be discriminated by using an infrared thermal image of one test specimen, but the abnormal portion and the sound portion cannot be discriminated by using an infrared thermal image of another test specimen, depending on the heat environment. A state of a damage in the surface layer of the structure can be guessed by comparing the infrared thermal image of the test specimen whose abnormal portion and sound portion can be discriminated, the infrared thermal image of the test specimen whose abnormal portion and sound portion cannot be discriminated, and the infrared thermal image of the structure.

A seventh aspect of the invention is a test specimen for infrared inspection, which is produced to represent a structure to be inspected for defects by using an infrared camera, comprising:

a plate member having a to-be-photographed surface which is an object to be photographed by an infrared camera, an attachment surface which is on a back side of the to-be-photographed surface and to be opposed to the structure, and an abnormal portion formed on the side of the attachment surface, and a heat conductive member to be adhered to the attachment surface of the plate member.

The test specimen of the seventh aspect of the invention is provided with the to-be-photographed surface which is the object to be photographed by the infrared camera, the attachment surface which is on the back side of the to-be-photographed surface and to be opposed to the structure, and the abnormal portion formed on the side of the attachment surface. The test specimen is attached to the structure such that the attachment surface is mutually opposed to a part of the to-be-inspected surface of the structure so as to be integral with the structure. The same heat conduction as that of the structure occurs in the test specimen.

According to an eighth aspect of the invention, the abnormal portion is a depression formed in a part of the attachment surface.

The eighth aspect of the invention relates to one embodiment of the abnormal portion formed on the test specimen. It is easy to produce the depression.

According to a ninth aspect of the invention, the abnormal portion is a gap formed in a surface layer of the attachment surface.

The ninth aspect of the invention relates to one embodiment of the abnormal portion to be formed on a test specimen.

According to a tenth aspect of the invention, a heat conductive member is adhered to the attachment surface.

When the heat conductive member is adhered to the attachment surface of the test specimen according to the tenth aspect of the invention, the heat conduction from the structure to the test specimen becomes smooth, and a degree of adhesion between the test specimen and the structure becomes high.

According to an eleventh aspect of the invention, the test specimen attaching step prepares the plate-shaped test specimen having the to-be-photographed surface and the attachment surface which is the back side of the to-be-photographed surface, and attaches the test specimen to the structure by opposing the to-be-inspected surface of the structure and the attachment surface of the test specimen to each other to form a partial gap which becomes the abnormal portion between the to-be-inspected surface of the structure and the attachment surface of the test specimen.

The first aspect of the invention is described with reference to the eleventh aspect of the invention.

As a preparatory stage of infrared inspection, the plate-shaped test specimen having the to-be-photographed surface and the attachment surface which is the back side of the to-be-photographed surface is prepared. And, the test specimen is attached to the structure with the to-be-inspected surface of the structure and the attachment surface of the test specimen opposed to each other. At this time, the partial gap is formed between the to-be-inspected surface of the structure and the attachment surface of the test specimen, and the partial gap is determined as the abnormal portion (test specimen attaching step).

In a case where the to-be-inspected surface of the structure is actually photographed by the infrared camera, the to-be-photographed surface of the test specimen is photographed by the infrared camera (test specimen photographing step).

In the to-be-photographed surface of the test specimen, when a difference between the surface temperature of the abnormal portion and the surface temperature of the sound portion other than the abnormal portion becomes large to a certain level, it becomes possible to discriminate between the surface of the abnormal portion and the surface of the sound portion by using the infrared thermal image of the photographed test specimen, and as a result, it becomes possible to discriminate the position of the abnormal portion (discriminating step).

In the time zone when it has become possible to discriminate the position of the abnormal portion, the to-be-inspected surface of the structure is photographed by the infrared camera (structure photographing step).

If the surface layer of the to-be-inspected surface of the structure has a damage, the position of the damage can be checked by using an infrared thermal image of the to-be-inspected surface.

According to a twelfth aspect of the invention, a heat conductive member having recesses and projections formed in the surface is used.

A thirteenth aspect of the invention is a heat conductive member which is interposed between a structure to be inspected for defects by an infrared camera and a test specimen produced to represent the structure and attached to the structure, to provide smooth heat conduction from the structure to the test specimen, in which recesses and projections are formed in the surface.

When the heat conductive member comes into contact with projected portions present on the surface of the structure, the surface of the contacted portion of the heat conductive member is deformed. If the heat conductive member has a flat surface, the surface of the heat conductive member is partly warped when the surface of the contacted portion is deflected, and a gap might be formed between the surface of the heat conductive member and the surface of the structure. Meanwhile, when the recesses and projections, for example grooves, are formed in the surface of the heat conductive member, the grooves absorb the deformation of the surface of the contacted portion, so that gaps are inhibited from occurring. As a result, the degree of adhesion of the heat conductive member to the surface of the structure becomes high.

Advantageous Effect of the Invention

According to the present invention, the test specimen is directly attached to the structure in a state that heat conduction becomes smooth between the test specimen and the structure, so that the heat environment of the test specimen can be substantially agreed with the heat environment of the structure. The test specimen reflects accurately the heat environment of the structure. Therefore, when a to-be-photographed surface of the test specimen is photographed by an infrared camera and an abnormal portion and a sound portion can be discriminated by using the infrared thermal image, it is seen that it is a time zone suitable for infrared inspection of a real structure.

BEST MODE FOR CARRYING OUT THE INVENTION

Embodiments of the invention are described below with reference to the drawings.

According to the embodiments, a test specimen representing a structure is directly attached to the structure to be inspected, the test specimen is photographed by an infrared camera, and the photographed infrared thermal image is analyzed to judge whether a heat environment of the structure is in a time zone suitable for infrared inspection. When it is judged that it is the time suitable for the inspection, the infrared inspection of the structure is performed.

The embodiments are divided into a first embodiment and a second embodiment below. The test specimen used in the first embodiment is called a first test specimen, and the test specimen used in the second embodiment is called a second test specimen in the following description.

First Embodiment

[Structure of First Test Specimen]

The first test specimen used for infrared inspection is described below.

FIGS. 1A and 1B show a structure of the first test specimen. FIGS. 2A and 2B show the first test specimen to which a heat conductive seat is adhered.

A test specimen 10 has a plate member 11. The plate member 11 has on its one surface a to-be-photographed surface 12 which is to be photographed by an infrared camera and on the back side an attachment surface 13 to be attached to the structure. A depression 14 corresponding to an abnormal portion is formed in the center of the attachment surface 13. A heat conductive seat 15 is adhered to a portion of the attachment surface 13 where the depression 14 is not formed.

As a material for the plate member 11, concrete or mortar is used. Alternatively, considering the thermal diffusivity of the concrete, a type of material different from the structure, such as natural rubber or the like which is lighter in weight than the concrete or the like, may be used. The heat conductive seat 15 is a member having a high thermal diffusion coefficient. The heat conductive seat 15 may be of any material or form if the heat conduction from the structure can be made smooth and if it serves to enhance a degree of adhesion to the surface of the structure. For example, a heat conductive grease may be used.

It is general that a heat conductive seat is used to adhere small parts such as electronic parts. Meanwhile, the test specimen 10 of this embodiment is larger in size and heavier than the electronic parts. Therefore, the heat conductive seat 15 of this embodiment is required to stick the test specimen 10 to the structure as equally and firmly as possible.

As shown in FIG. 22, when plural grooves 15a are formed at regular intervals in the heat conductive seat 15, a degree of adhesion of the heat conductive seat 15 to the surface of the structure becomes high. The surface of the structure is not flat but has a large number of recessed and projected portions. When the heat conductive seat 15 comes into contact with the projected portions, the surface of the contacted portion of the heat conductive seat 15 is deformed. If the heat conductive seat 15 has a flat surface, the surface of the heat conductive seat 15 is partly warped when the surface of the contacted portion is deformed, and there is a possibility of forming a gap between the surface of the heat conductive seat 15 and the surface of the structure. Meanwhile, the grooves 15a absorb the deformation of the surface of the contacted portion, so that a gap is inhibited from occurring. As a result, the degree of adhesion of the heat conductive seat 15 to the surface of the structure becomes high, whereby the grooves 15a contribute to the achievement of the purpose of the present invention, which is that the heat environment of the structure to be inspected can be grasped accurately even when complex conditions overlap in the infrared inspection. Holes may be formed instead of the grooves 15a in the heat conductive seat 15. In short, it is appropriate as far as the recesses and projections equivalent to the grooves 15a are formed in the surface of the heat conductive seat 15, and the formed shape does not matter if the deformation of the contacted portion can be absorbed. But, if the recesses and projections are excessively large, the recessed portions themselves may form gaps, so that it is necessary to appropriately adjust the degree and interval of the recesses and projections.

The test specimen means the plate member 11 itself in a narrow sense and, in a broad sense, it means an assembly comprising the plate member 11 and a set of members for attaching the plate member 11 to the structure. In this embodiment, the plate member 11 itself, or the plate member 11 having the heat conductive seat 15 adhered thereto is called the test specimen 10.

Each part of the test specimen 10 is determined to have an appropriate size. The present inventors formed the depression 14 having a length and a width of 100 mm and a depth of 2 mm in the plate member 11 having a length and a width of 300 mm and a thickness of 22 mm. And the heat conductive seat 15 having a thickness of about 1 mm was adhered to the attachment surface 13. The thickness of the plate member 11 has a certain preferable range. If it is excessively thick, the heat conduction from the attachment surface 12 to the to-be-photographed surface 11 takes time, and if it is excessively thin, the plate member 11 is brittle. Besides, it is also necessary to consider the thickness from a bottom surface 14a of the depression 14 to the to-be-photographed surface 12.

FIGS. 3A and 3B show a structure of a test specimen of an embodiment different from the test specimen of FIG. 1.

The test specimen 10' has a plate member 11'. It has a to-be-photographed surface 12' which is to be photographed by an infrared camera on one surface of the plate member 11', and an attachment surface 13', which is opposed to the structure, on the back side of the one surface. A gap 14' corresponding to the abnormal portion is formed in the center of the surface layer of the attachment surface 13'. And, an unshown heat conductive seat is adhered to the entire surface of the attachment surface 13'.

According to the present invention, either form of the test specimen 10 of FIGS. 1 and 2 or the test specimen 10' of FIGS. 3A and 3B is appropriate but the test specimen 10 of FIGS. 1 and 2 is preferable from the viewpoint of easiness of production and strength thereof. The following description is made as a case where the test specimen 10 of FIGS. 1 and 2 is used.

[Method of Attaching First Test Specimen to Structure]

FIGS. 4A to 4C show a state that the test specimens are attached to a structure. FIG. 4A schematically shows an overall view of the structure, FIG. 4B shows in a magnified form one of the test specimens of FIG. 4A, and FIG. 4C shows a state that the test specimen of FIG. 4B is viewed from below.

As shown in FIG. 4A, a structure 20 described here comprises a floor slab (including overhanging floor slabs) 21 which is disposed on a girder of a steel bridge and a wall parapet 22 which is connected to an overhang of the floor slab 21. A floor slab undersurface (including an in-girder floor slab undersurface and undersurfaces of east and west overhanging floor slabs) 23 of the floor slab 21 and an exterior surface 24 of the east and west wall parapets 22 are surfaces subject to the infrared inspection. Therefore, the floor slab undersurface 23 of the floor slab 21 and the exterior surface 24 of the east and west wall parapets 22 are provided with the test specimens 10 respectively. A method of attaching the test specimens 10 to the structure 20 is described with reference to the test specimens 10 attached to the floor slab undersurface 23 of the floor slab 21.

As shown in FIG. 4B, the test specimen 10 is attached to the floor slab 21 with the attachment surface 13 of the plate member 11 opposed to the to-be-inspected surface of the structure 20, namely the floor slab undersurface 23 of the floor slab 21. The heat conductive seat 15 is interposed between the attachment surface 13 of the test specimen 10 and the floor slab undersurface 23. A test specimen fixing frame 17 is attached to the peripheral edge of a portion of the floor slab undersurface 23, which is opposed to the attachment surface 13 of the test specimen 10. The test specimen fixing frame 17 has base portions 17a and pressing portions 17b. The base portions 17a are fixed to the floor slab undersurface 23 by a double-sided tape 18 (or a concrete glue). The pressing portions 17b are contacted to the to-be-photographed surface 12 of the test specimen 10 to press the test specimen 10 against the floor slab 21.

In this embodiment, the test specimen 10 and the floor slab 21 are adhered tightly without a gap (excluding the depression 14) with the heat conductive seat 15 between them so that the test specimens 10 and the floor slab 21 form an integral structure. And, heat conduction becomes smooth between the attachment surface 13 of the test specimen 10 and the floor slab undersurface 23. Besides, the depression 14 of the test specimen 10 is covered with the floor slab undersurface 23 to form an artificial abnormal portion, namely the gap 14'.

As another embodiment, the attachment surface 13 of the test specimen 10 may be directly contacted to the floor slab undersurface 23, but it is necessary to take measures not to form a gap as much as possible between the attachment surface 13 of the test specimen 10 and the floor slab undersurface 23. As still another embodiment, the base portion 17a of the test specimen fixing frame 17 may be fixed to the floor slab undersurface 23 with bolts.

The heat conductive seat 15 has functions to provide smooth heat conduction from the structure to the test specimen 10 and to enhance the degree of adhesion between the test specimen 10 and the structure, and it may also have a function to make the test specimen 10 adhere to the structure. When the heat conductive seat 15 being adhesive is used, the configuration becomes simple because the test specimen fixing frame 17 is not required. Meanwhile, use of the test specimen fixing frame 17 makes it unlikely that the test specimen 10 drops.

[Results of Temperature Measurement of Test Specimen and its Peripheral Area]

The present inventors attached a test specimen to a real structure and measured the temperatures of the test specimen and its peripheral area. FIG. 5 shows temperature measurement positions of the test specimen and its peripheral area. In this temperature measurement, the test specimen was attached to the floor slab undersurface of the steel bridge shown in FIG. 4A, and the temperatures of the test specimen and its peripheral area were measured.

In this temperature measurement, the temperatures at the positions indicated in FIG. 5, namely:
a temperature of an abnormal portion surface A of the test specimen 10,
a temperature of a sound portion surface B of the test specimen 10,
a temperature of an undersurface C of a floor slab 21,
a temperature of a position D 5 cm below the undersurface of the temperature floor slab 21, and
an outside air temperature E (not shown)
were measured. The results of the temperature measurement at the respective positions are shown in FIG. 6.

It is seen from FIG. 6 that a temperature change of the test specimen 10 has nothing to do with a change of the outside air temperature and is substantially same as the temperature change of the floor slab 21. And, when it is sunny during daytime, a temperature difference of a certain level or higher (−0.2° C. or more) occurs between the abnormal portion surface A and the sound portion surface B of the test specimen 10 during nighttime, but when it is cloudy during daytime, a temperature difference of a certain level or higher (−0.2° C. or more) does not occur between the abnormal portion surface A and the sound portion surface B of the test specimen 10 throughout the day even if there is a difference of the outside air temperature. This phenomenon indicates that the test specimen 10 is influenced by the indirect effect.

In other words, when it is sunny during daytime, the top surface of the floor slab 21 is warmed by solar radiation, and the heat conduction occurs from the top surface to the undersurface of the floor slab 21 when the temperature lowers during nighttime. The heat is conducted to the test specimen 10 and reaches the sound portion surface B but not to the abnormal portion surface A because of heat insulation by the abnormal portion. Therefore, it is considered that the abnormal portion surface A has a temperature lower than the sound portion surface B, and the temperature difference between the abnormal portion surface A and the sound portion surface B becomes large. Meanwhile, when it is cloudy during daytime, the top surface of the floor slab 21 is not warmed by solar radiation, and the heat conduction from the top surface to the undersurface of the floor slab 21 does not occur when the temperature drops during nighttime. Accordingly, it is considered that the test specimen 10 is not influenced by the indirect effect, and as a result, the temperature difference between the abnormal portion surface A and the sound portion surface B becomes small.

[Heat Environment 1 of Structure]

To prove the advantage of the test specimen 10 according to the embodiment shown in FIG. 1, etc., a heat environment of a concrete box-girder bridge, which is one example of the structure, is described below.

FIG. 7 shows an overview of a heat environment of a concrete box-girder bridge. A box girder 30 has a floor slab 31 including an overhang, a lower flange 33 and a web 32 (showing one side only) connected to the floor slab 31 and the lower flange 33, and the floor slab 31, the lower flange 33 and the web 32 form a space 34 within the box girder 30. When the floor slab 31 receives the solar radiation, heat is accumulated in the space 34. The heat accumulated in the space 34 is hard to escape, and the space 34 is often in a high-temperature state.

As shown in FIG. 7, the floor slab 31, the lower flange 33 and the web 32 of the box girder 30 receives heat from air and also receives heat from solar radiation and the space 34. Thus, it is considered that since the floor slab 31, the lower flange 33 and the web 32 are in the situation to receive heat from the front and back surfaces, they are influenced by the indirect effect. The conventional test specimens used in the above-described Patent References 1 and 2 do not reflect the influence of the indirect effect. Therefore, when the conventional test specimens are used to perform the infrared inspection of the box girder 30, an optimal inspection time might not be able to be judged accurately. Meanwhile, the test specimen 10 according to this embodiment shown in FIG. 1 and the like reflects the influence of the indirect effect. Therefore, when the test specimen 10 is used to perform the infrared inspection of the box girder 30, the optimal inspection time can be judged accurately.

FIG. 8 shows the results of thermal analysis of the box girder, and the measured or estimated results of the outside air temperature, the surface temperature of the web 32 and the estimation temperature of the space 34 are shown. FIG. 8 shows the analysis results of a time when the daily range of the outside air temperature, namely a difference between the minimum atmosphere temperature and the maximum atmosphere temperature in a day, is small.

Even when the change of the outside air temperature is small as shown in FIG. 8, the space 34 is warmed when the floor slab 31 of the box girder 30 receives solar radiation, so that the temperature of the space 34 becomes higher than the outside air temperature. For example, the temperature of the web 32 warmed by the heat of the space 34 has become higher than the outside air temperature in the time zone t1 of FIG. 8. Thus, the heat conduction occurs in the lower flange 33 and the web 32 from inside to outside of the box in the time zone t1. Therefore, the surface of an abnormal portion 42 included in the lower flange 33 has a temperature lower than the surface around it. And, the surface of an abnormal portion 43 included in the web 32 has a temperature lower than the surface around it. Therefore, it is possible to detect the abnormal portion by the infrared inspection in the time zone t1.

Meanwhile, the outside air temperature rises in the time zone t2 of FIG. 8 and becomes higher than or substantially equal to the temperature of the web 32. In the time zone t2, the heat conduction occurs in the lower flange 33 and the web 32 in the direction from inside to outside of the box and in the opposite direction, or the heat conduction does not occur. Therefore, it is not likely that the temperature difference generates on the surface of the abnormal portion 42 included in the lower flange 33 and the surface around it. And, it is not likely that the temperature difference generates on the surface of the abnormal portion 43 included in the web 32 and the surface around it. Therefore, in the time zone t2, it is hard to detect the abnormal portion by the infrared inspection.

Heat is given to the conventional test specimen mainly by the outside air temperature. When a change of the outside air temperature is small as shown in FIG. 8, the temperature difference between the abnormal portion surface and the sound portion surface is hardly produced on the conventional test specimen. Therefore, when the conventional test specimen is used, it is judged that "the infrared inspection cannot be made" even if there is generated a temperature difference that the surfaces of the abnormal portions 41 to 43 of the box girder 30 can be discriminated by the indirect effect by using the infrared thermal image as in the time zone t1 of FIG. 8. Thus, when the conventional test specimen is used, the heat environment of the box girder cannot be grasped accurately.

Meanwhile, the test specimen 10 of this embodiment can make the substantially same heat conduction as that of the box girder 30 even when the change of the outside air temperature is small as in FIG. 8. Therefore, when the test specimen 10 is used, the heat environment of the box girder can be grasped accurately.

FIG. 9 shows a state that the test specimens are attached to the box girder. As an analysis result by the present inventors, what is considered to be the best is to attach the test specimen 10 to the undersurfaces of overhangs 31a and 31b of the floor slab 31, the undersurface of the lower flange 33 and the side walls of the webs 32 in order to grasp the heat environment of the box girder 30.

[Heat Environment 2 of Structure]

It is natural that the test specimen 10 can be used to grasp the heat environment of not only the structure having a small member-thickness but also the structure having a large member-thickness. Here, the heat environment of the hollow slab bridge as one example of the structure having a large member-thickness is described below.

FIG. 10 shows the results of measuring the temperatures of a test specimen directly attached to the hollow slab bridge and a test specimen disposed near the hollow slab bridge. In this temperature measurement, the test specimen according to this embodiment is attached to the floor slab undersurface of the hollow slab bridge, and this test specimen is called a new test specimen in the following description. In this temperature measurement, the conventional test specimen is placed in an instrument shelter which is disposed near the hollow slab bridge, and this test specimen is called a conventional test specimen in the following description. The abnormal portion of the new test specimen and the abnormal portion of the conventional test specimen are formed to have the same size and the same depth.

According to FIG. 10, the difference of the abnormal portion surface temperature and the sound portion surface temperature of the new test specimen and the difference of the abnormal portion surface temperature and the sound portion surface temperature of the conventional test specimen are substantially same. Thus, it seems that the new test specimen has substantially the same heat environment observation tendency as the conventional test specimen does.

When the sound portion surface temperature of the conventional test specimen and the sound portion surface temperature of the new test specimen are compared on the basis of the temperature of the floor slab undersurface as a reference, the sound portion surface temperature of the new test specimen is closer to the temperature of the floor slab undersurface. Therefore, it is seen that the heat environment of the floor slab undersurface can be grasped more accurately when the new test specimen is used than when the conventional test specimen is used.

There is a difference, though it is slight, between the new test specimen and the conventional test specimen in timing that the difference between the abnormal portion surface temperature and the sound portion surface temperature is produced. It is considered that this is because the heat environment of the new test specimen is closer to the heat environment of the floor slab as a result that the new test specimen is integral with the floor slab.

Thus, when it is assumed that the hollow slab bridge is inspected, the temperature change of the new test specimen has the same changing tendency as the temperature change of the conventional test specimen. In addition, since the temperature change of the new test specimen follows the temperature change of the hollow slab bridge more closely than the temperature change of the conventional test specimen, it can be said that the heat environment of the hollow slab bridge can be grasped more accurately when the new test specimen is used.

[Procedure of Infrared Inspection]

A procedure of the infrared inspection of this embodiment is described with reference to FIGS. 1A and 1B, FIGS. 4A, 4B and 4C, FIGS. 11A and 11B and FIGS. 12A and 12B. FIG. 11A is an actual infrared thermal image of the test specimen, and FIG. 11B shows FIG. 11A schematically. FIG. 12A is a real infrared thermal image of a structure, and FIG. 12B shows FIG. 12A schematically.

As a preparatory stage of the infrared inspection, the test specimen 10 described with reference to FIGS. 1A and 1B is produced, and the test specimen is attached to the to-be-inspected surface (floor slab undersurface 23 in FIGS. 4A and 4B) of the structure 20 in the manner as described with reference to FIGS. 4A, 4B and 4C.

To actually photograph the floor slab undersurface 23 of the structure 20 by an infrared camera, the to-be-photographed surface 12 of the test specimen 10 is photographed by the infrared camera. In the surface temperature of the to-be-photographed surface 12 of the test specimen 10, when a difference between the surface temperature of the abnormal portion and the surface temperature of the sound portion excluding the abnormal portion increases to a certain level, a surface 12a of the gap and a surface 12b of the sound portion have a different appearance in the infrared thermal image of the photographed test specimen 10 as shown in FIGS. 11A and 11B, so that it becomes possible to discriminate between the abnormal portion and the sound portion. The time zone that the abnormal portion and the sound portion of the test specimen 10 can be discriminated by using the infrared thermal image is a time zone that the heat environment of the to-be-inspected surface of the structure 20 is suitable for the infrared inspection. In that time zone, the floor slab undersurface 23 of the structure 20 is photographed by the infrared camera. If the surface layer of the floor slab undersurface 23 has a damage, there is a difference between the appearance of a damaged surface 23a and the appearance of another surface in the infrared thermal image of the floor slab undersurface 23 as shown in FIGS. 12A and 12B. Therefore, the damage position can be discriminated by using the infrared thermal image of the floor slab undersurface 23.

[Application Example of Infrared Inspection]

The infrared inspection of this embodiment can be applied as follows. Description is made with reference to FIGS. 1A and 1B and FIGS. 4A, 4B and 4C.

Plural test specimens each having a different size are prepared. For example, plural test specimens 10 are produced with their thickness from the bottom surface 14a of the depression 14 to the to-be-photographed surface 12 and the depth of the depression 14 varied, and the test specimens are attached to the to-be-inspected surface (floor slab undersurface 23 in FIG. 4) of the structure 20 as described with reference to FIGS. 4A, 4B and 4C.

There is a possibility that when the to-be-photographed surface 12 of the each test specimen 10 is photographed by an infrared camera, an abnormal portion and a sound portion can be discriminated by using an infrared thermal image of one test specimen 10, but an abnormal portion and a sound portion cannot be discriminated by using an infrared thermal image of another test specimen 10. In this situation, when the structure 20 is photographed by the infrared camera, it is possible to detect an abnormality which is the same as the one test specimen 10 where the abnormal portion and the sound portion can be discriminated, but it is not possible to detect another abnormality which is the same as said another test specimen 10 where the abnormal portion and the sound portion cannot be discriminated. From a different viewpoint, it can be said that this is a situation that a state of an abnormal portion within the structure 20, for example, a depth from the floor slab undersurface 23 to the abnormal portion, a thickness of the abnormal portion itself or the like can be seen.

Therefore, when the infrared thermal image of said each test specimen 10 and the infrared thermal image of the structure 20 are compared, a state of a damage in the surface layer of the structure 20 can be guessed.

Second Embodiment

[Structure of Second Test Specimen]

The second test specimen used for infrared inspection is described below.

FIGS. 18A and 18B show the second test specimen having the heat conductive seat adhered.

A test specimen 50 has a plate member 51. It has a to-be-photographed surface 52, which is to be photographed by an infrared camera, on one surface of the plate member 51, and an attachment surface 53, which is opposed to the structure, on the back side of the one surface. The attachment surface 53 of the plate member 51 is flat unlike the attachment surface 13 of the plate member 11 shown in FIG. 1. A heat conductive seat 55 is adhered to the edge portion excluding the center portion of the attachment surface 53.

The material for the plate member 51 may be same as that for the plate member 11 shown in FIGS. 1A and 1B. The heat conductive seat 55 may be same as the heat conductive seat 15 shown in FIGS. 1A and 1B. Similarly to the heat conductive seat 15, it is desirable that grooves or holes are formed in the heat conductive seat 55.

Each part of the test specimen 50 is determined to have an appropriate size. The present inventors formed the plate members 51 in three types each having a length and a width of 300 mm and having a thickness of 10, 20, 30 mm respectively. The heat conductive seat 55 having thickness of about 1 mm was adhered to the attachment surface 53. The thickness of the heat conductive seat 55 is appropriately determined depending on the thickness of an abnormal portion to be formed.

[Method of Attaching Second Test Specimen to Structure]

FIGS. 19A and 19B show a state that the test specimen is attached to a structure. FIG. 19A shows a state that the test specimen is attached to the structure, and FIG. 19B shows a state of the test specimen of FIG. 19A viewed from below. FIGS. 19A and 19B are diagrams corresponding to FIGS. 4B and 4C. Therefore, in FIGS. 19A and 19B, the same component part corresponding to that (floor slab undersurface 23) of FIGS. 4A, 4B and 4C is denoted by the same reference numeral, and its description is omitted.

As shown in FIG. 19A, the test specimen 50 is attached to the floor slab 21 to have an attachment surface 53 of the plate member 51 directed to face the to-be-inspected surface of the structure 20, namely the floor slab undersurface 23 of the floor slab 21. The heat conductive seat 55 is interposed between the floor slab undersurface 23 and the edge portion of the attachment surface 53 excluding the center portion of the test specimen 50. Meanwhile, a gap 56 having a depth equivalent to the thickness of the heat conductive seat 55 is formed between the center portion of the attachment surface 53 of the test specimen 50 and the floor slab undersurface 23. A test specimen fixing frame 60 is attached to the peripheral edge of a portion of the floor slab undersurface 23, which is opposed to the attachment surface 53 of the test specimen 50.

The test specimen fixing frame 60 has a lower frame 61, an upper frame 63 and bolts 65.

As shown in FIG. 20A, the lower frame 61 comprises four L-shaped frame members 61a to 61d, and each of frame members 61a to 61d is arranged to form a square frame. The inner edge of the lower frame 61 is larger than the outer edge of the test specimen 50. Plural lower holes 62 are formed in the surface of the lower frame 61. In this embodiment, two lower holes 62 are formed in each of the frame members 61a to 61d. The back surfaces of the frame members 61a to 61d are fixed to the floor slab undersurface 23 by a double-sided tape 68 (or a concrete glue).

As shown in FIG. 20B, the upper frame 63 is formed of a square frame member. The inner edge of the upper frame 63 is smaller than the inner edge of the lower frame 61 and the outer edge of the test specimen 50. The upper frame 63 is formed with plural bolt holes 64 which are formed from the front to back surfaces. In this embodiment, eight bolt holes 64 are formed.

The fixing bolts 65 are inserted through the bolt holes 64 formed in the upper frame 63 from below to upward of the floor slab undersurface 23 and threaded into the lower holes 62 formed in the lower frame 61.

Since the fixing bolts 65 are threaded into the lower holes 62, the upper frame 63 is contacted to the edge portion of the to-be-photographed surface 52 of the test specimen 50 to press the test specimen 50 against the floor slab 21. A thermal insulation material 67 is interposed between the upper frame 63 and the test specimen 50. The thermal insulation material 67 may be an adhesive material.

In this embodiment, the test specimen 50 and the floor slab 21 are adhered tightly without a gap (excluding the center portion of the attachment surface 53) with the heat conductive seat 55 between them so that the test specimen 50 and the floor slab 21 form an integral structure. And, heat conduction becomes smooth between the attachment surface 53 of the test specimen 50 and the floor slab undersurface 23. Besides, an artificial abnormal portion, namely the gap 56, is formed by the attachment surface 53 of the test specimen 50, the floor slab undersurface 23, and the heat conductive seat 55.

As shown in FIGS. 19A and 19B, two temperature loggers 71 and 72 are attached to the upper frame 63 in this embodiment. The temperature logger 71 receives periodically signals from a temperature sensor 73 for measuring a surface temperature of the abnormal portion in the surface temperature of the to-be-photographed surface 52 of the test specimen 50 and a temperature sensor 74 for measuring a surface temperature of the sound portion excluding the abnormal portion in the surface temperature of the to-be-photographed surface 52 of the test specimen 50, and accumulates the temperature data. The temperature logger 72 receives periodically signals from a temperature sensor 75 for measuring the temperature of the floor slab undersurface 23 and a temperature sensor 76 for measuring the ambient temperature of the floor slab undersurface 23 (for example, the atmosphere temperature about 5 cm below the floor slab undersurface 23), and accumulates the temperature data.

As shown in FIG. 21, one end of a wire 78 is joined to the upper frame 63, and the unshown other end of the wire 78 is joined to a handrail or the like of the structure 20 in this embodiment. Besides, one end of a wire 79 is buried in the plate member 51, and the other end of the wire 79 is joined to the wire 78. Even if the upper frame 63 is disconnected from the lower frame 61, the upper frame 63 and the plate member 51 are prevented from falling by the wires 78 and 79.

In the second embodiment, the test specimen fixing frame 17 of the first embodiment may be used instead of the test specimen fixing frame 60. Conversely, in the first embodiment, the test specimen fixing frame 60 of the second embodiment may be used instead of the test specimen fixing frame 17.

In the second embodiment, the same results as those in the first embodiment shown in FIG. 6 can also be obtained. A temperature change of the test specimen 50 has nothing to do with a change of the outside air temperature and is substantially same as the temperature change of the floor slab 21. And, when it is sunny during daytime, a temperature difference of a certain level or higher occurs between the abnormal portion surface and the sound portion surface of the test specimen 50 during nighttime, but when it is cloudy during daytime, a temperature difference of a certain level or higher does not occur between the abnormal portion surface and the sound portion surface of the test specimen 50 throughout the day even if there is a difference in outside air temperature. This phenomenon indicates that the test specimen 50 is influenced by the indirect effect The [procedure of infrared inspection] and [application example of infrared inspection] of the second embodiment are same as in the first embodiment, so that their descriptions are omitted.

In the second embodiment, the test specimen 50 has a simple structure in comparison with the first embodiment, so that the test specimen 50 can be produced easily.

Meanwhile, since the heat conductive seat 15 of the first embodiment may be thin in comparison with the second embodiment, the material for the heat conductive seat 15 can be saved.

INDUSTRIAL APPLICABILITY

The present invention can be used for not only infrared inspection of a structure using concrete, such as a bridge, an elevated ridge, etc., but also defect inspection of a general structure using a material, such as mortar, in which a failure may occur.

LIST OF REFERENCE NUMERALS

Figure 1A:
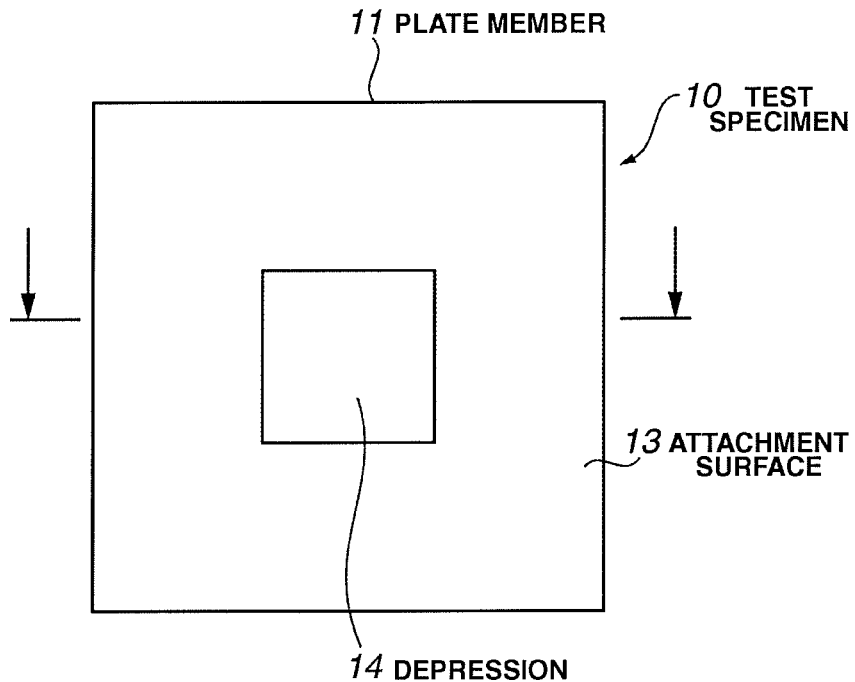
FIG. 1A is a plan view showing a structure of a first test specimen.
Figure 1B:
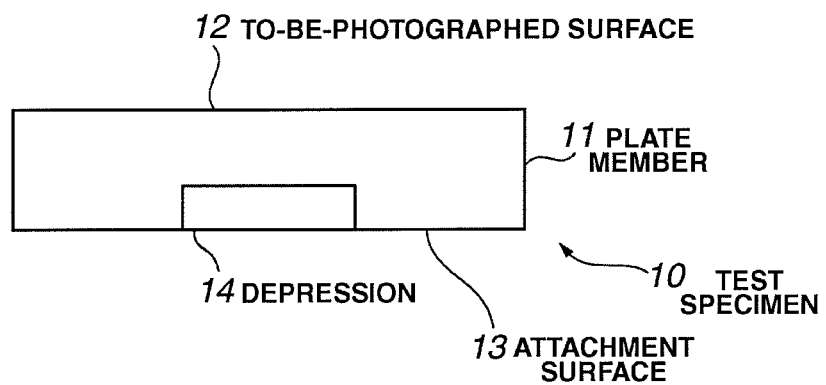
FIG. 1B is a sectional view.
Figure 2A:
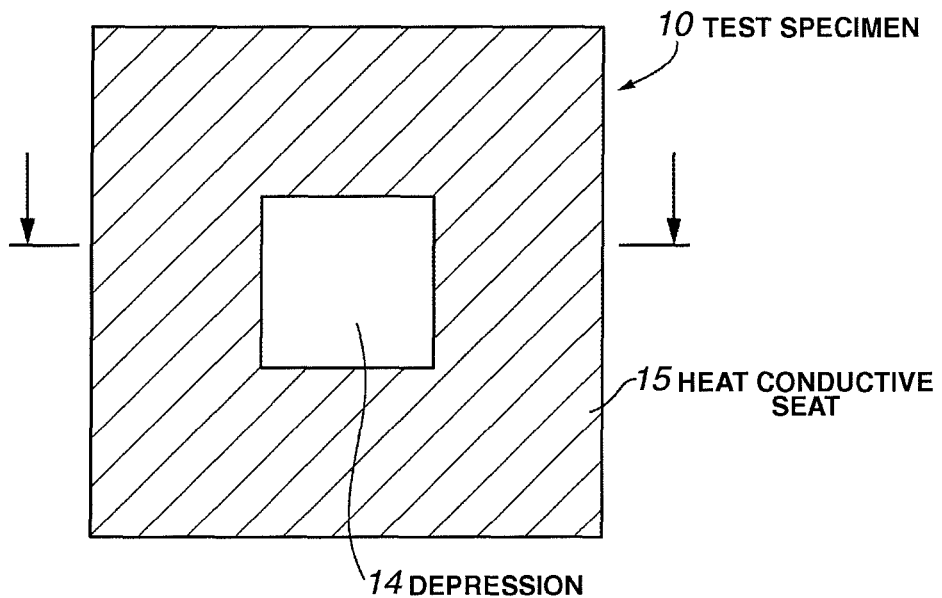
FIG. 2A is a plan view of the first test specimen to which a heat conductive seat is adhered.
Figure 2B:
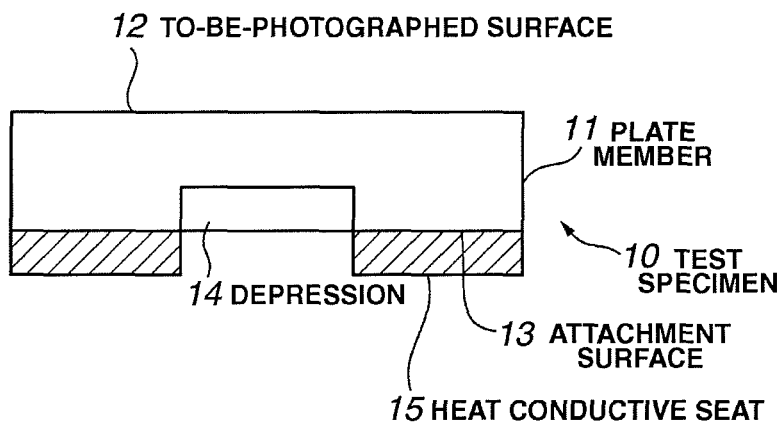
FIG. 2B is a sectional view thereof.
Figure 3A:
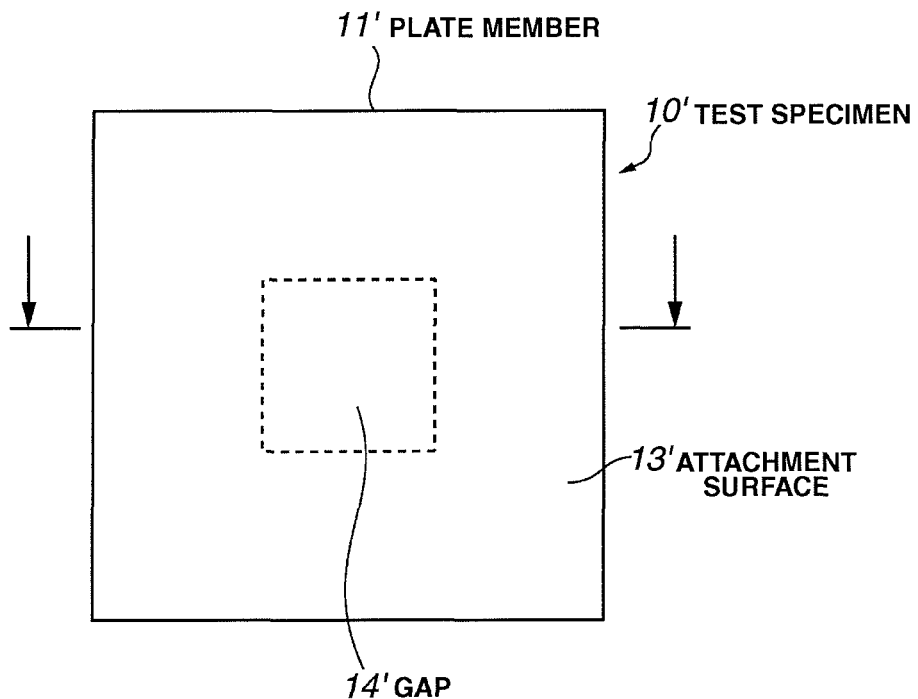
FIG. 3A is a plan view showing a structure of a test specimen of an embodiment different from the test specimen of FIGS. 1A and 1B.
Figure 3B:
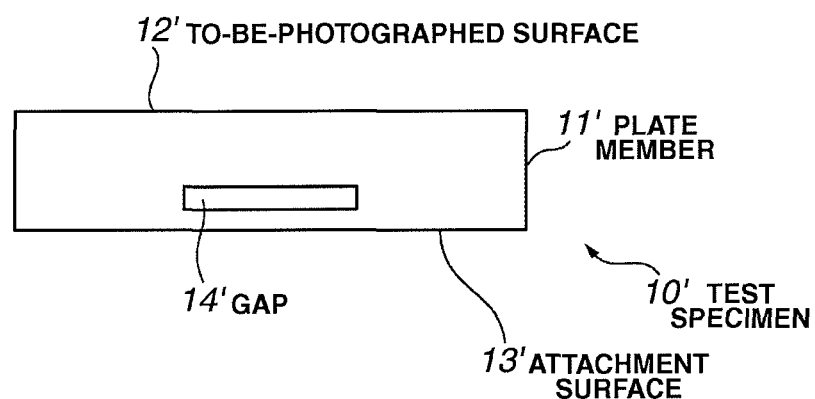
FIG. 3B is a sectional view thereof.
Figure 4A:
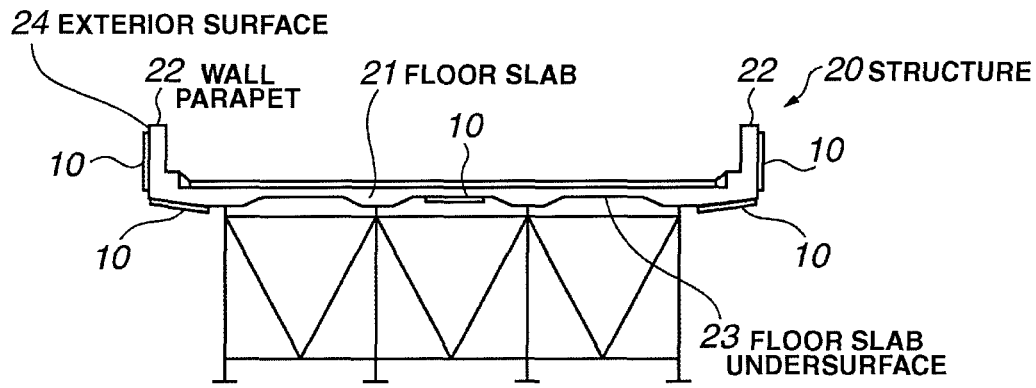
FIG. 4A is a diagram schematically showing a structure.
Figure 4B:
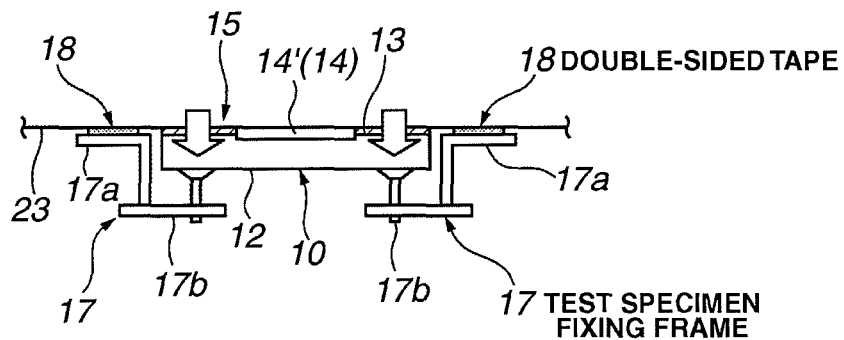
FIG. 4B is a diagram showing in a magnified form a part of the test specimens of FIG. 4A.
Figure 4C:
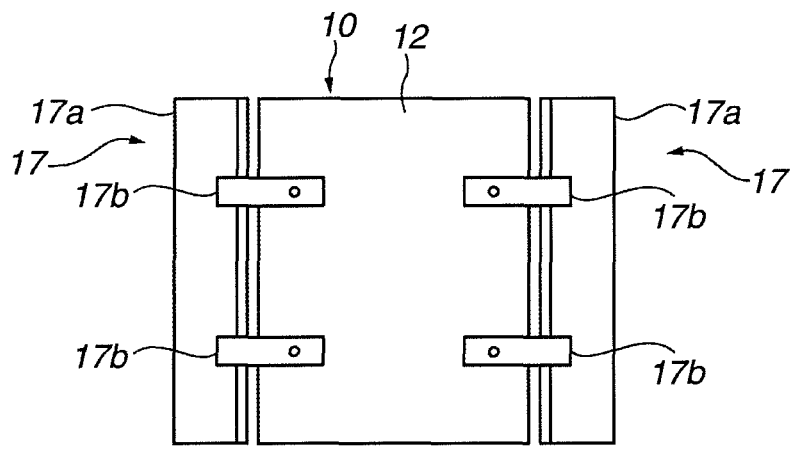
FIG. 4C is a diagram showing a state of the test specimen of FIG. 4B viewed from below.
Figure 5:
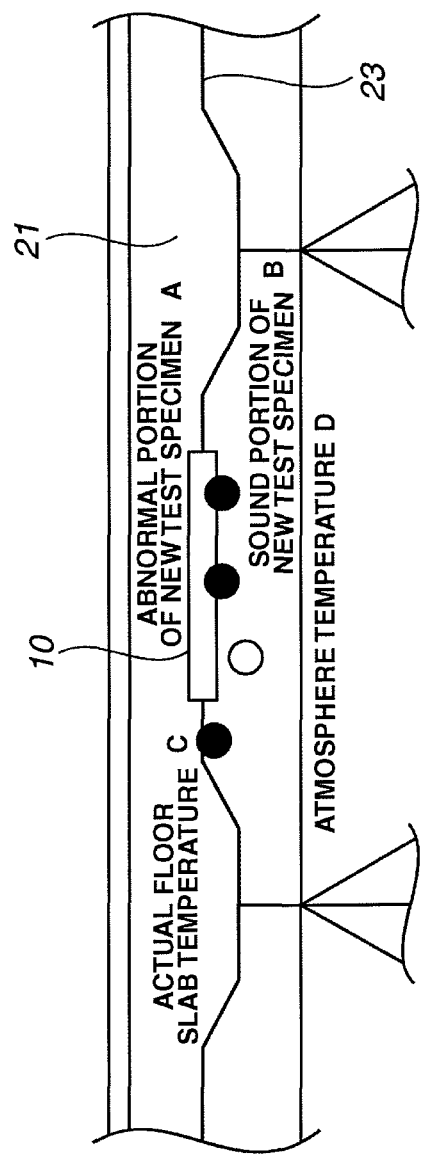
FIG. 5 is a diagram showing temperature measurement positions of the test specimen and its peripheral area.
Figure 6:
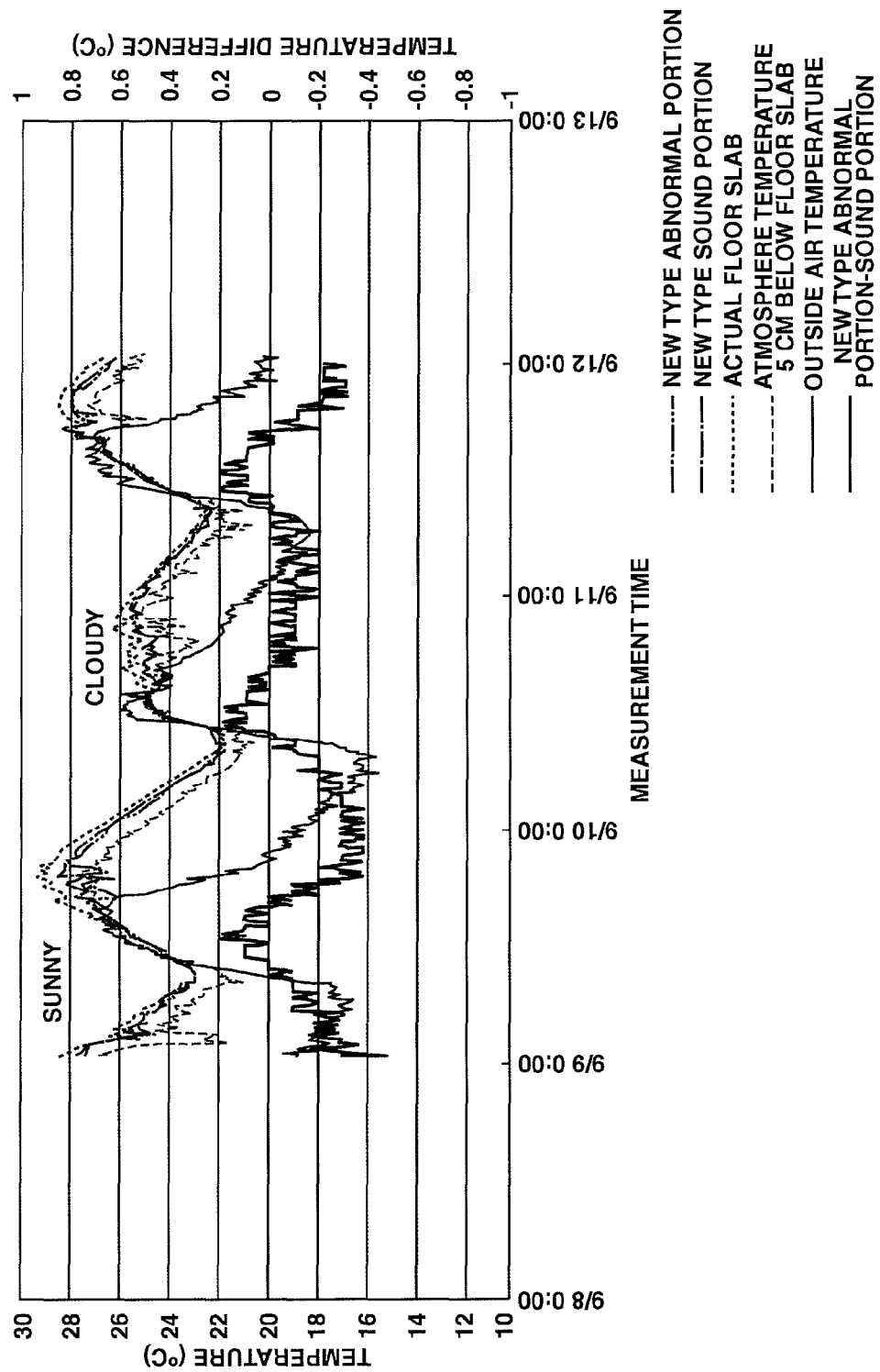
FIG. 6 is a diagram showing the results at temperature measurement positions of the test specimen and its peripheral area.
Figure 7:
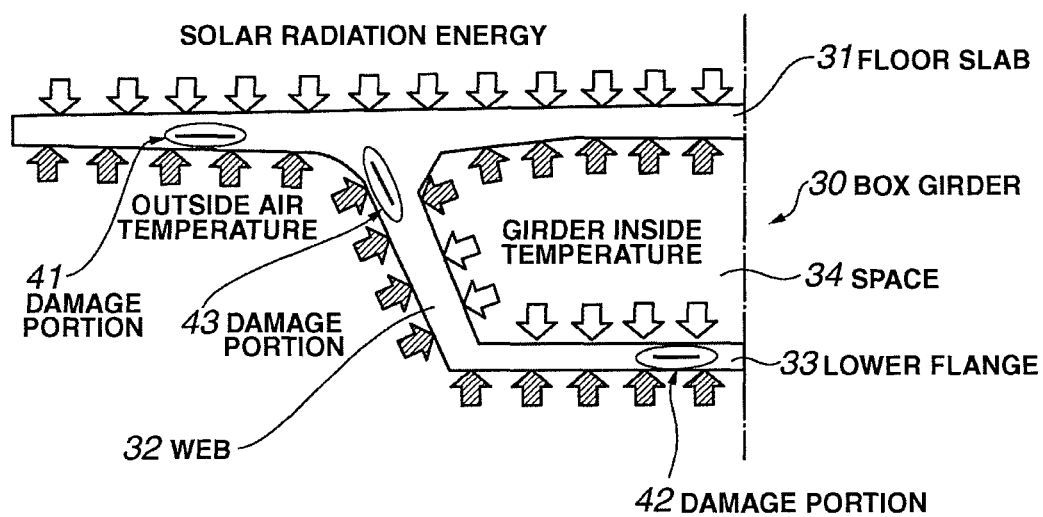
FIG. 7 is a diagram showing an overview of a heat environment of a concrete box-girder bridge.
Figure 8:
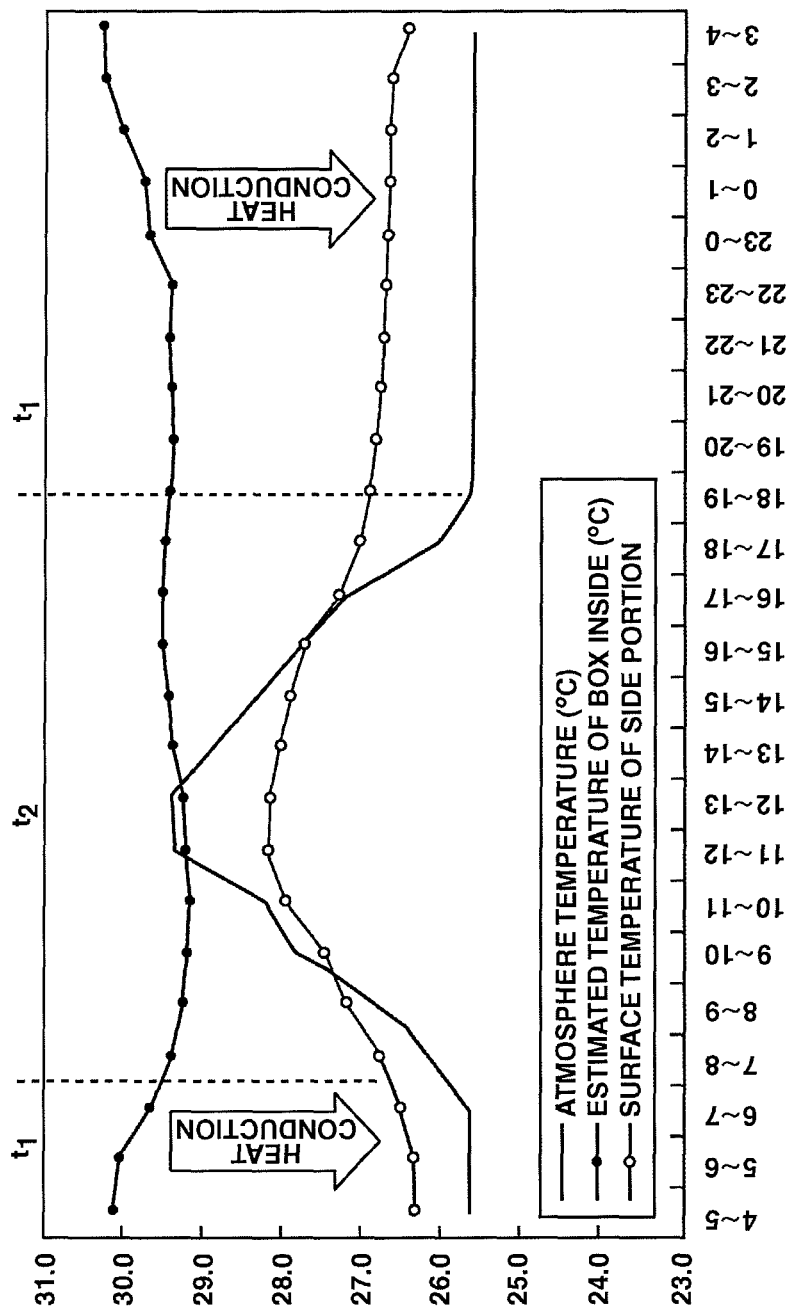
FIG. 8 is a diagram showing the results of thermal analysis of a box girder.
Figure 9:
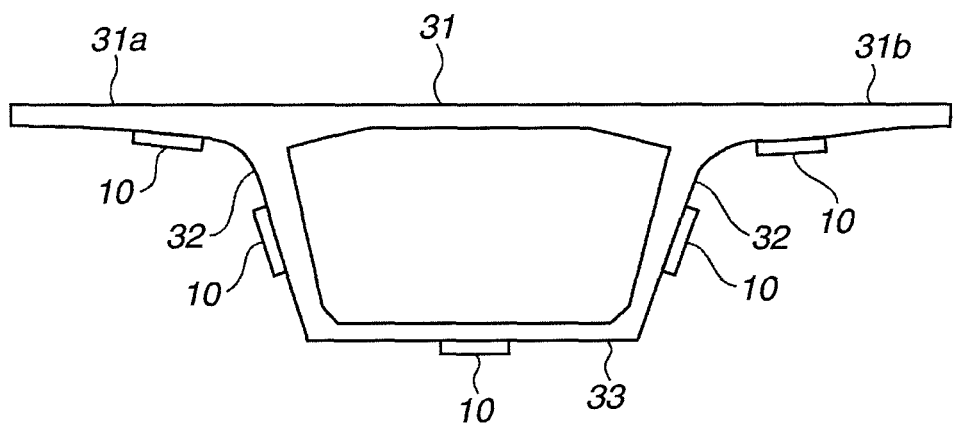
FIG. 9 is a diagram showing a state that test specimens are attached to a box girder.
Figure 10:
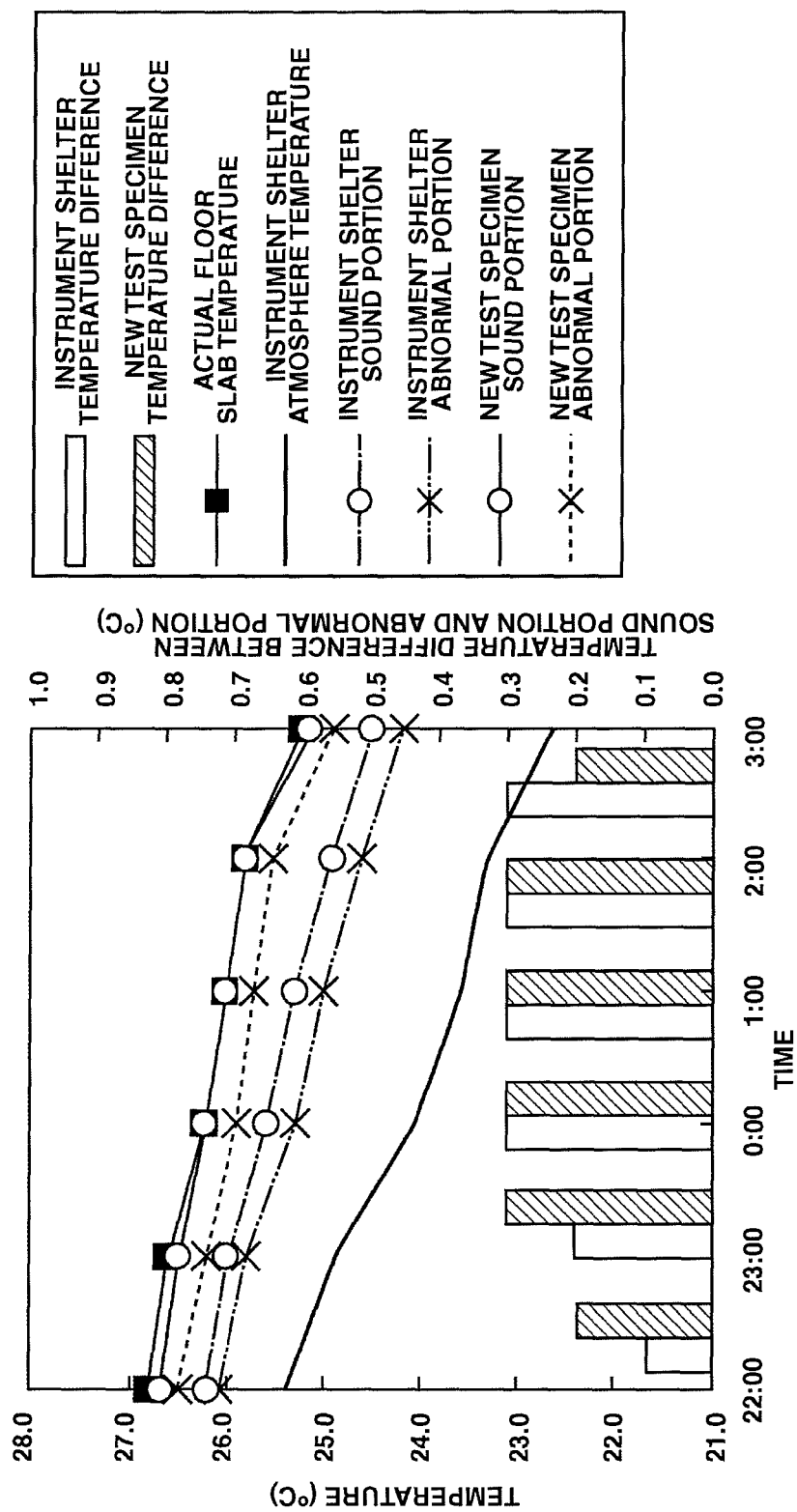
FIG. 10 is a diagram showing the results of temperature measurement of test specimens directly attached to a hollow slab bridge and test specimens disposed near the hollow slab bridge.
Figure 11A:
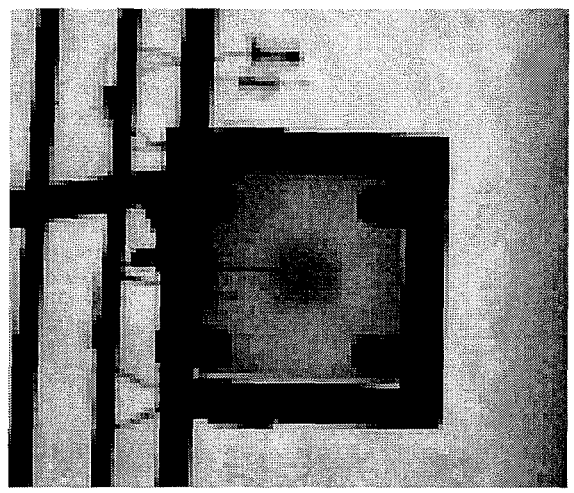
FIG. 11A is an infrared thermal image of a test specimen.
Figure 11B:
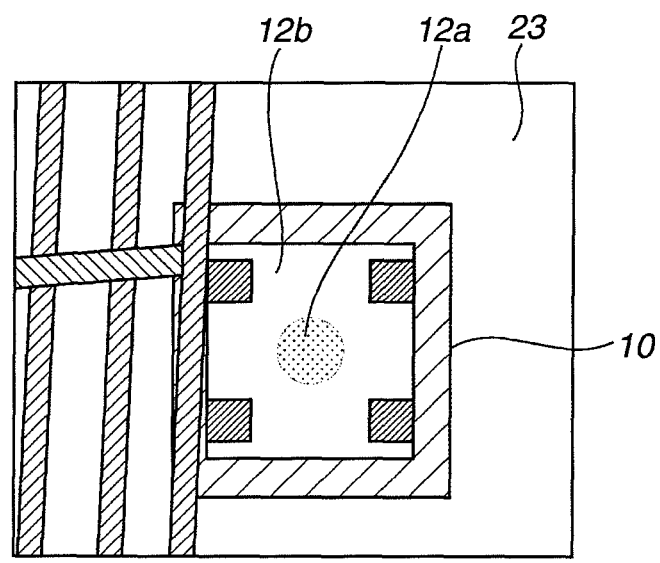
FIG. 11B is a schematic diagram of FIG. 11A.
Figure 12A:
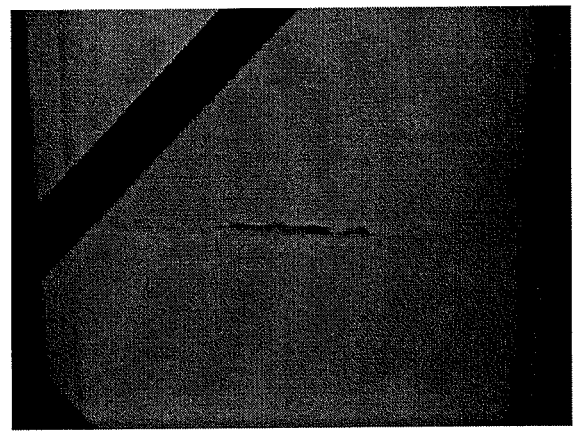
FIG. 12A is an infrared thermal image of a structure.
Figure 12B:
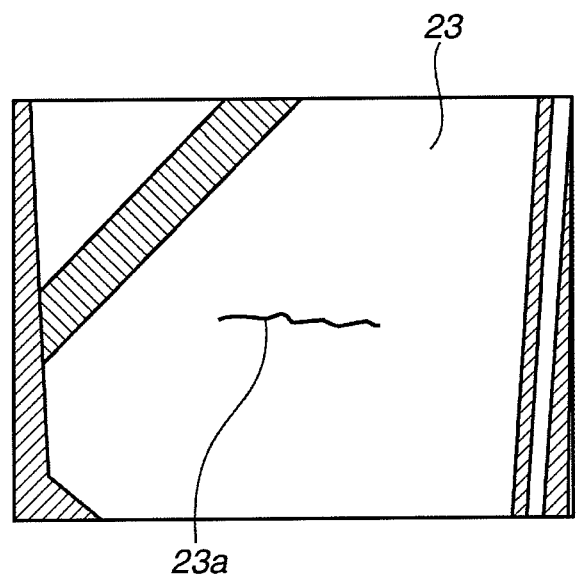
FIG. 12B is a schematic diagram of FIG. 12A.
Figure 13:
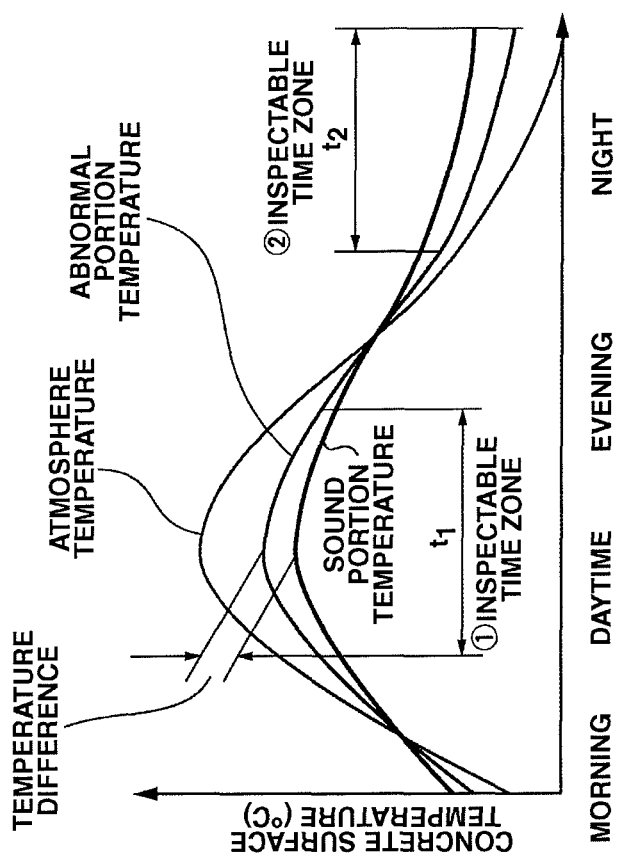
FIG. 13 is a diagram showing changes of the atmosphere temperature, a surface temperature of a sound portion of a structure and a surface temperature of an abnormal portion of the structure.
Figure 14A:
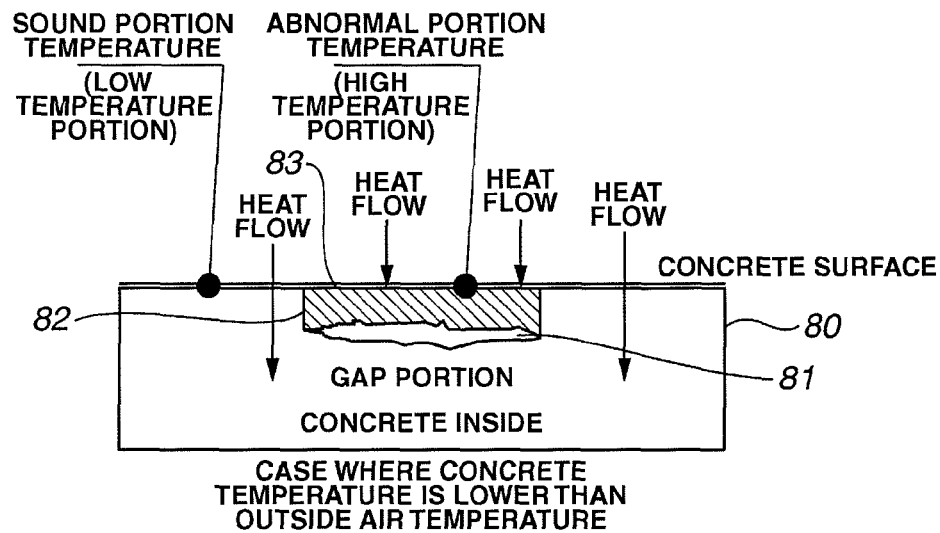
FIG. 14A and FIG. 14B are diagrams showing a concept of a phenomenon that a temperature difference is produced.
Figure 14B:
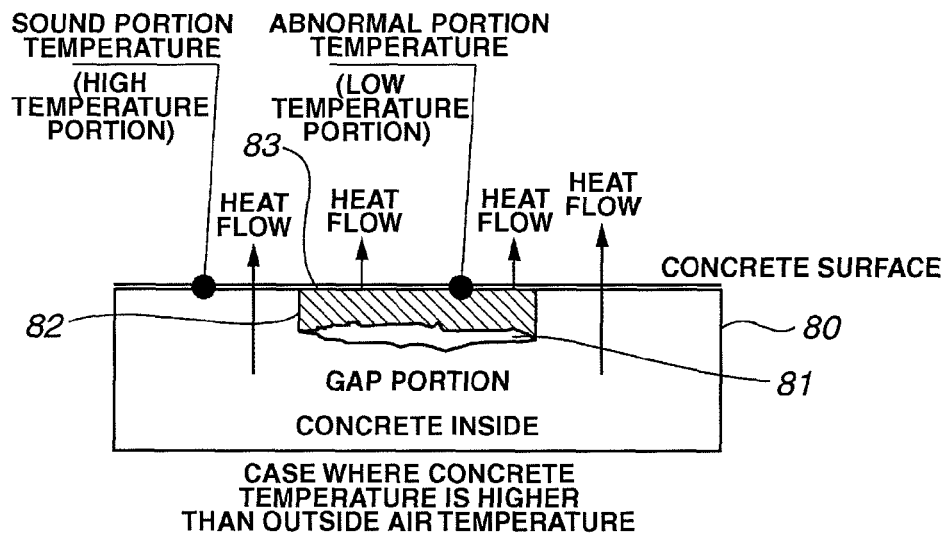
Figure 15:
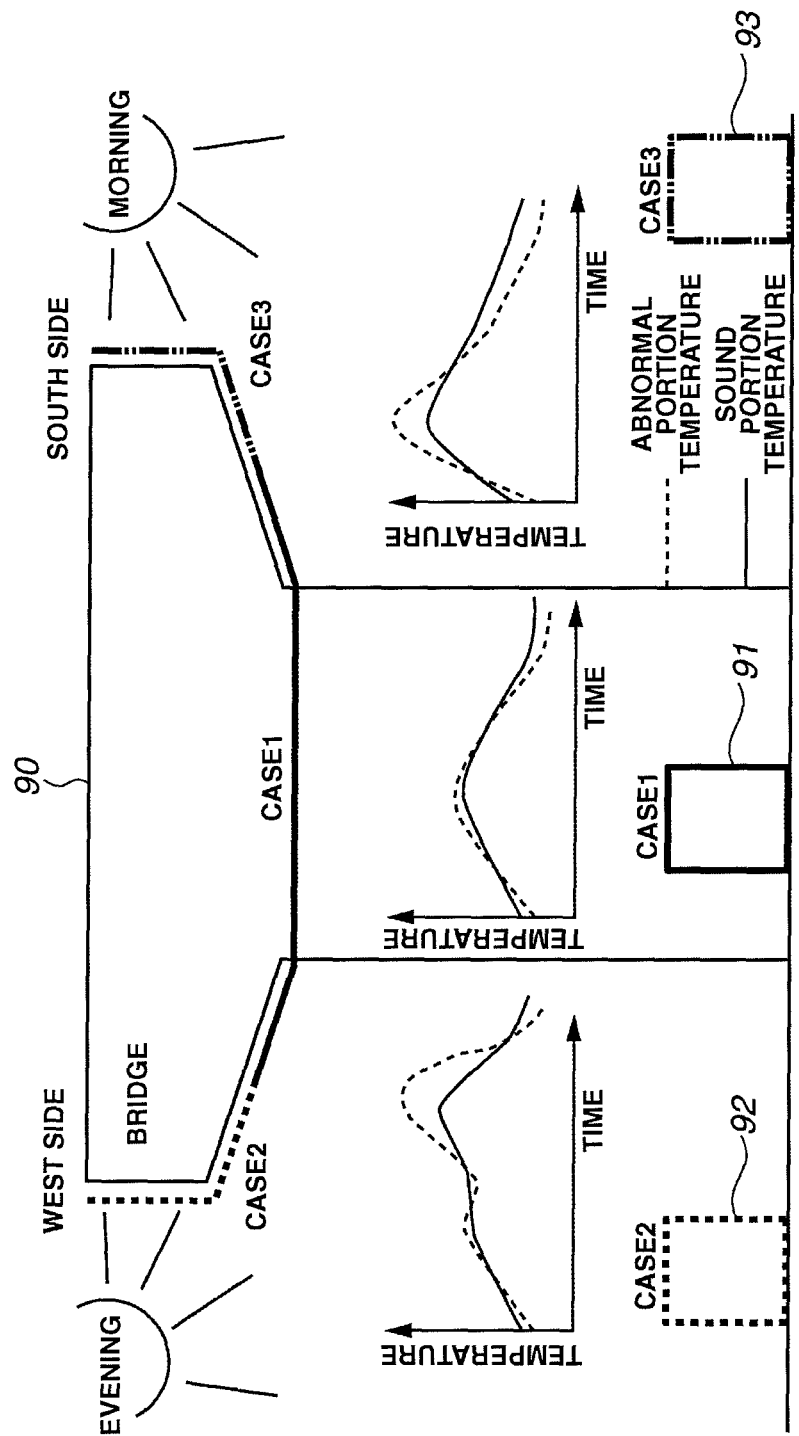
FIG. 15 is a diagram showing a state of a heat environment estimation method using conventional test specimens.
Figure 16:
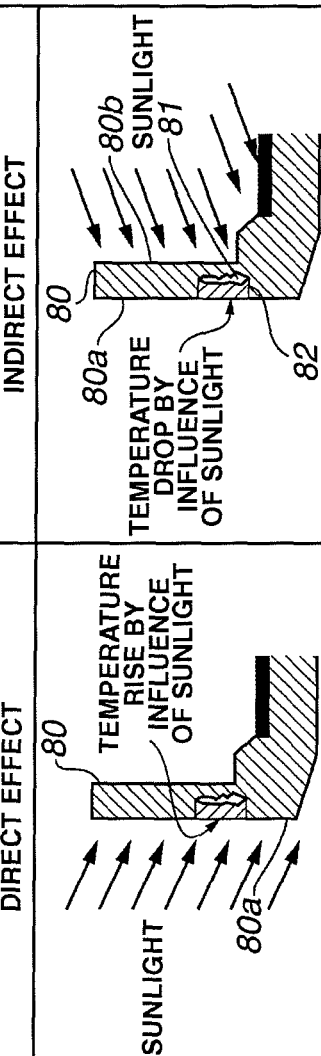
FIG. 16 is a diagram showing a concept of a direct effect and an indirect effect.
Figure 17A:
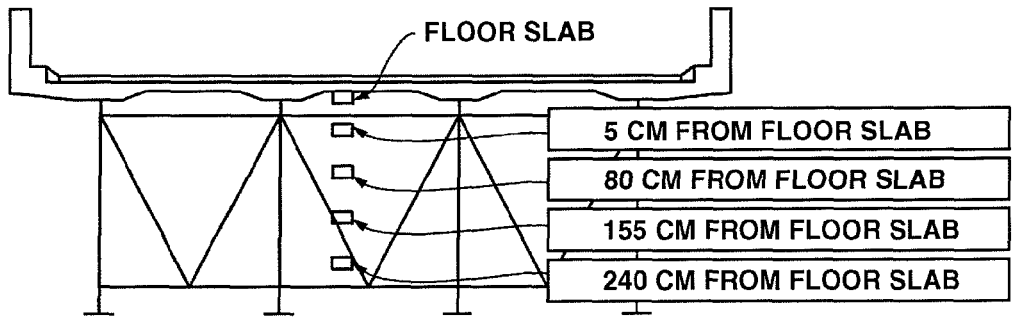
FIG. 17A is a diagram showing a temperature measurement position of a steel bridge having a concrete floor slab.
Figure 17B:
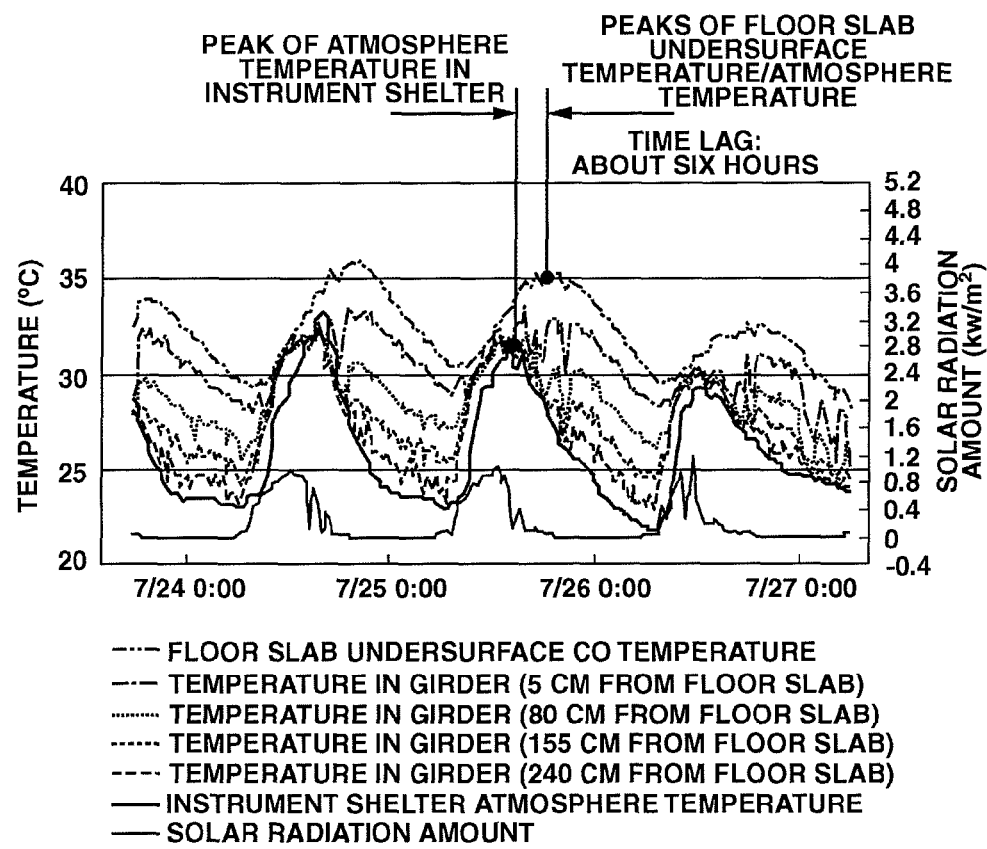
FIG. 17B is a diagram showing temperature measurement of FIG. 17A.
Figure 18A:
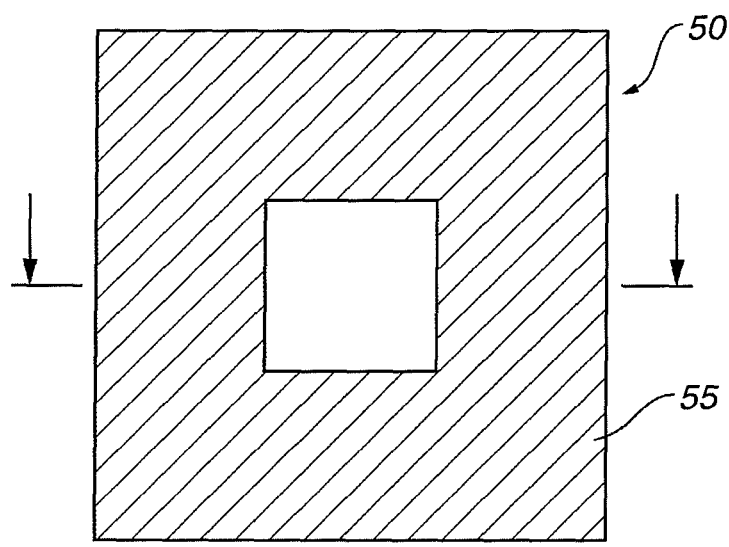
FIG. 18A is a plan view of a second test specimen to which a heat conductive seat is adhered.
Figure 18B:
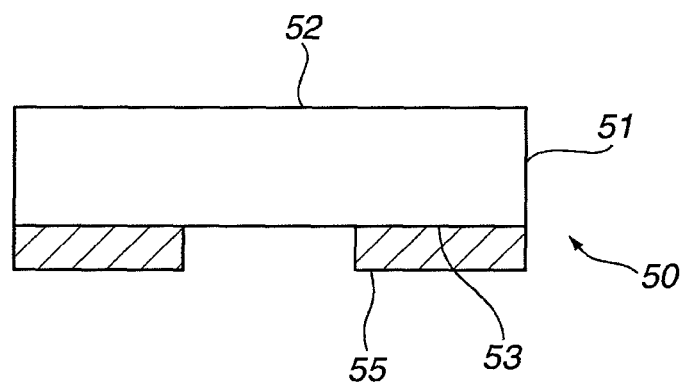
FIG. 18B is a sectional view thereof.
Figure 19A:
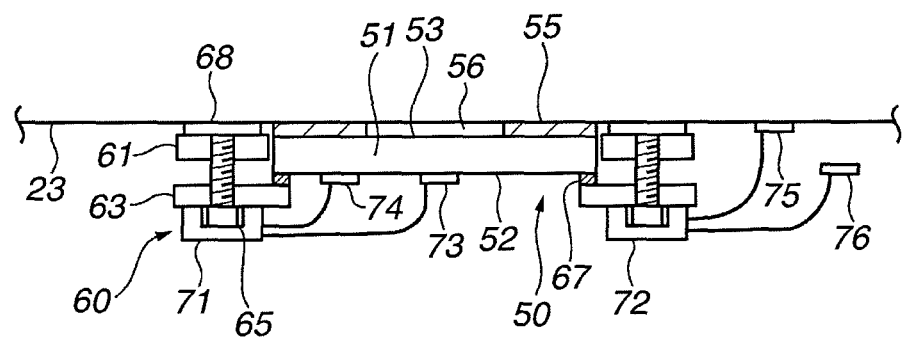
FIG. 19A is a diagram showing a state that a test specimen is attached to a structure.
Figure 19B:
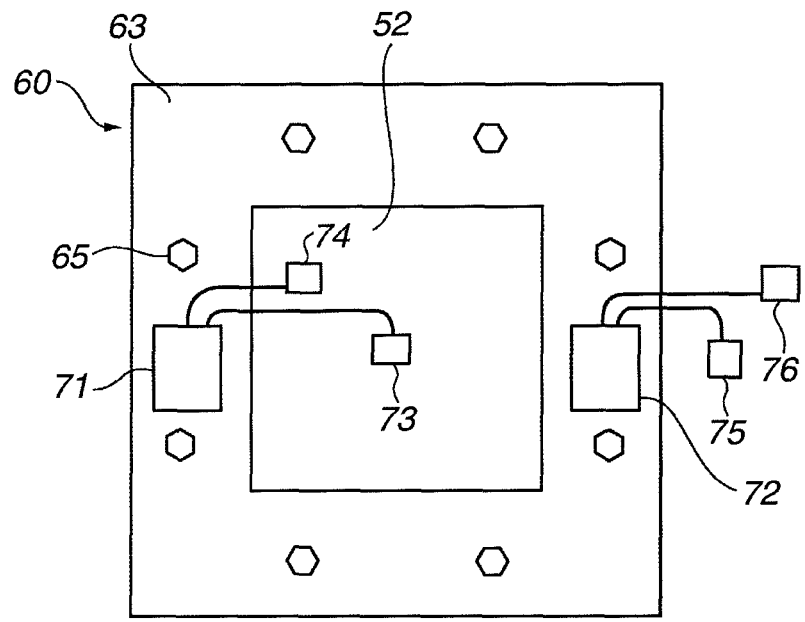
FIG. 19B is a diagram showing a state that the test specimen is viewed from below.
Figure 20A:
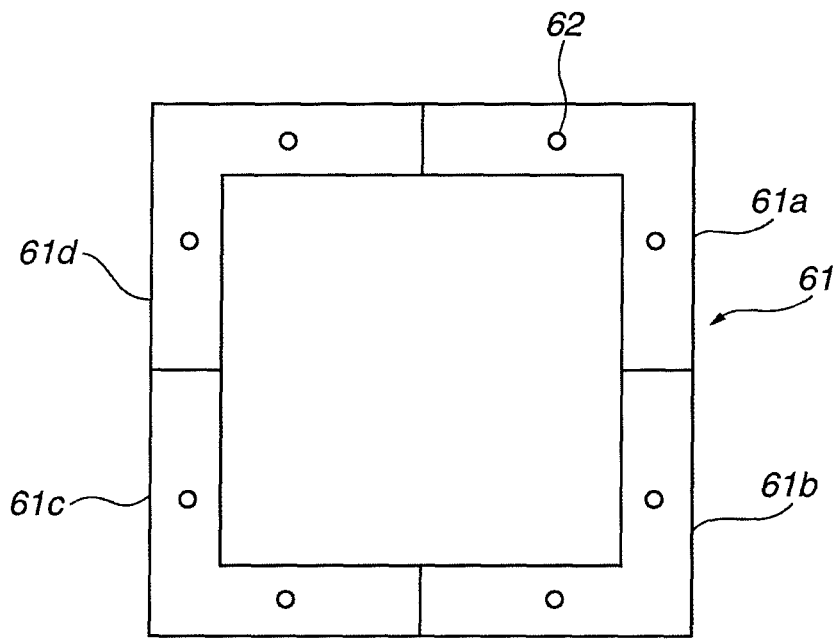
FIG. 20A is a plan view of a lower frame of a test specimen fixing frame.
Figure 20B:
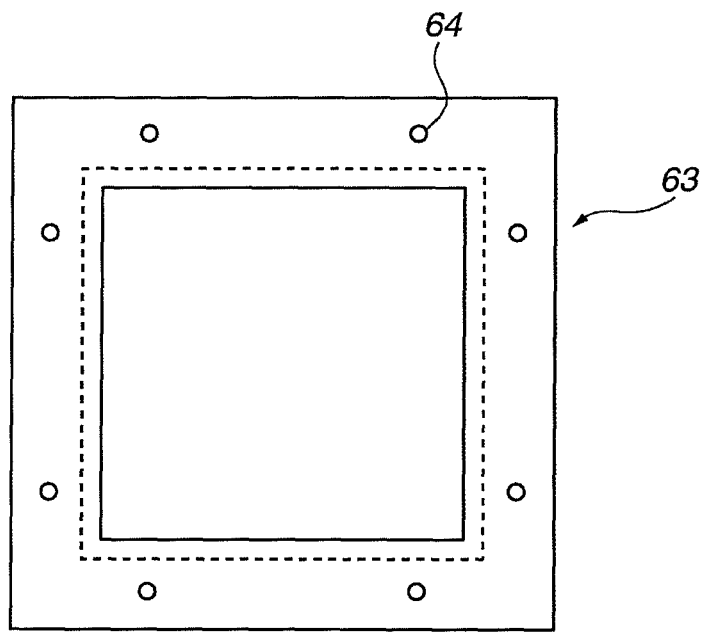
FIG. 20B is a plan view of an upper frame of the test specimen fixing frame.
Figure 21:
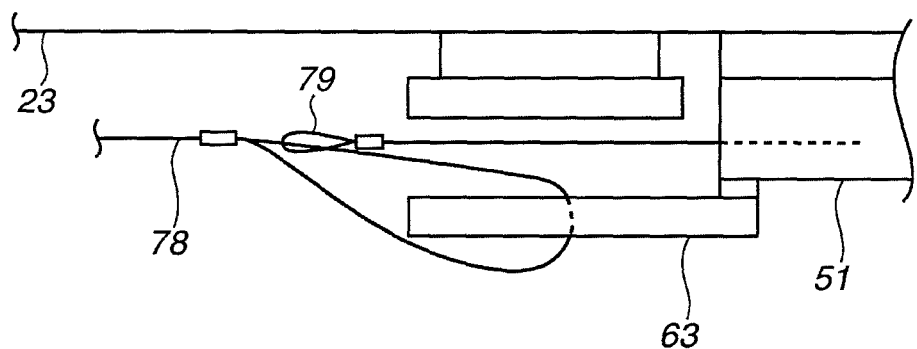
FIG. 21 is a diagram showing a test specimen, a test specimen fixing frame and a wire.
Figure 22:
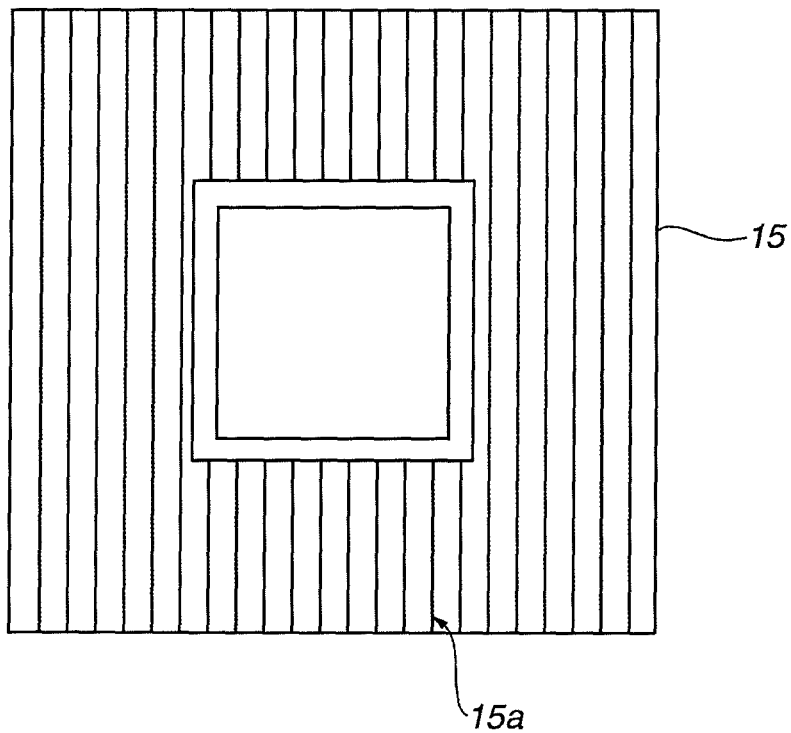
FIG. 22 is a plan view showing a heat conductive seat in which grooves are formed.

10: test specimen, 11: plate member, 12: to-be-photographed surface, 13: attachment surface, 14: depression, 15: heat conductive seat, 20: structure, 21: floor slab, 22: wall parapet, 23: floor slab undersurface, 24: exterior surface.

The invention claimed is:

1. A method of infrared inspection of inspecting a structure for defects by using an infrared camera, comprising:
   a test specimen attaching step of preparing a plate-shaped test specimen having a to-be-photographed surface and an attachment surface which is a back side of the to-be-photographed surface, attaching the test specimen to the structure with a to-be-inspected surface of the structure and the attachment surface of the test specimen opposed to each other, and providing an artificial abnormal portion forming a gap between surface of the structure and the test specimen;
   a test specimen photographing step of photographing the to-be-photographed surface of the test specimen by the infrared camera;
   a discriminating step of discriminating between the surface of the abnormal portion and the surface of a sound portion excepting the abnormal portion on the to-be-photographed surface of the test specimen by using an infrared thermal image of the test specimen; and
   a structure photographing step of photographing the to-be-inspected surface of the structure by the infrared camera in a time zone in which it is capable of discriminating between the surface of the abnormal portion and the surface of the sound portion.

2. The method of infrared inspection of inspecting structure according to claim 1, wherein the test specimen attaching step interposes a heat conductive member having a hole between the to-be-inspected surface of the structure and the attachment surface of the test specimen, and attaches the test specimen to the structure so that the hole forms a gap of a thickness of the heat conductive member between the to-be-inspected surface of the structure and the attachment surface of the test specimen.

3. The method of infrared inspection of inspecting a structure according to claim 1, therein the test specimen comprises:
   a plate member having a to-be-photographed surface which is an object to be photographed by the infrared camera, an attachment surface which is on a back side of the to-be-photographed surface and to be opposed to the structure, and a depression formed on the side of the attachment surface, and
   a heat conductive member to be adhered to the attachment surface of the plate member.

4. The method of infrared inspection of inspecting a structure according to claim 1, wherein a heat conductive member is provided between the to-be-inspected surface of the structure and the attachment surface of the test specimen, the heat conductive member having recesses and projections formed on the surface thereof.

5. The method of infrared inspection of inspecting a structure according to claim 1, wherein the test specimen attaching step prepares the plate-shaped test specimen having the to-be-photographed surface and the attachment surface which is the back side of the to-be-photographed surface wherein a depression corresponding to the abnormal portion is formed in the attachment surface, and attaches the test specimen to the structure with the to-be-inspected surface of the structure and the attachment surface of the test specimen opposed to each other.

6. The method of infrared inspection of inspecting a structure according to claim 5, wherein the structure conducts heat received by a back side of the to-be-inspected surface to the to-be-inspected surface.

7. The method of infrared inspection of inspecting a structure according to claim 5, wherein the test specimen attaching step attaches plural test specimens each having a different state of the abnormal portion to the structure.

8. The method of infrared inspection of inspecting a structure according to claim 5, wherein the test specimen attaching step interposes a heat conductive member between the to-be-inspected surface of the structure and the attachment surface of the test specimen.

9. The method of infrared inspection of inspecting a structure according to claim 8, wherein a heat conductive member having recesses and projections formed in the surface thereof is used.

* * * * *